United States Patent
Yang et al.

(10) Patent No.: US 9,884,884 B2
(45) Date of Patent: Feb. 6, 2018

(54) **COMPOUND EXTRACTED FROM HUSK AND FRUIT STEM OF *XANTHOCERAS SOBIFOLIA* AND ITS EXTRACTING METHOD AND USE THEREOF**

(76) Inventors: Baizhen Yang, Liaoning (CN);
Songjian Wang, Liaoning (CN);
Congfu Zhao, Liaoning (CN)

( * ) Notice: Subject to any disclaimer, the term of this patent is extended or adjusted under 35 U.S.C. 154(b) by 2944 days.

(21) Appl. No.: 11/631,637

(22) PCT Filed: Jul. 5, 2005

(86) PCT No.: PCT/CN2005/000988
§ 371 (c)(1),
(2), (4) Date: Jan. 5, 2007

(87) PCT Pub. No.: WO2006/002602
PCT Pub. Date: Jan. 12, 2006

(65) Prior Publication Data
US 2008/0058273 A1   Mar. 6, 2008

(30) Foreign Application Priority Data
Jul. 7, 2004 (CN) .......................... 2004 1 0020921

(51) Int. Cl.
*C07H 15/24* (2006.01)
*A61K 31/7034* (2006.01)
*C07J 63/00* (2006.01)
*A23L 33/105* (2016.01)

(52) U.S. Cl.
CPC ............ *C07H 15/24* (2013.01); *A23L 33/105* (2016.08); *C07J 63/00* (2013.01); *A23V 2002/00* (2013.01)

(58) Field of Classification Search
USPC .......................................... 514/33; 536/18.1
See application file for complete search history.

(56) References Cited

U.S. PATENT DOCUMENTS

| | | | |
|---|---|---|---|
| 6,616,943 B2 | 9/2003 | Wang | |
| 7,524,824 B2 * | 4/2009 | Chan et al. | 514/33 |
| 2003/0091669 A1 | 5/2003 | Wang | |
| 2003/0096030 A1 | 5/2003 | Wang et al. | |
| 2004/0146591 A1 | 7/2004 | Wang | |
| 2005/0220910 A1 * | 10/2005 | Chan et al. | 424/769 |

FOREIGN PATENT DOCUMENTS

| | | |
|---|---|---|
| CN | 1081369 | 2/1994 |
| CN | 1081369 A | 2/1994 |
| CN | 1092991 A | 10/1994 |
| CN | 1092992 A | 10/1994 |
| CN | 1349820 | 5/2002 |
| CN | 1413724 | 4/2003 |
| CN | 21413724 | 4/2003 |
| WO | WO 2005 037200 | 4/2005 |

OTHER PUBLICATIONS

English Translation of IPER for PCT/CN2005/000988 mailed Jul. 2, 2005.
Yingjie Chen et al., 1985, "Studies on the Constituents of Xanthoceras sorbifolia Bunge. V. Major Saponins from the Fruits of Xanthoceras sorbifolia Bunge," Chemical & Pharmaceutical Bulletin, 33(4): 1387-1394.

* cited by examiner

*Primary Examiner* — Leigh C Maier
(74) *Attorney, Agent, or Firm* — Smith, Gambrell & Russell, LLP

(57) ABSTRACT

This invention relates to the compound extracted from husk and fruit stem of *Xanthoceras Sobifolia* and its extracting method and use thereof. Its chemical structure is as below:

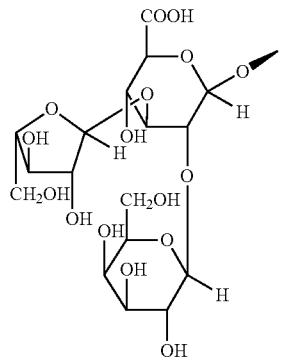
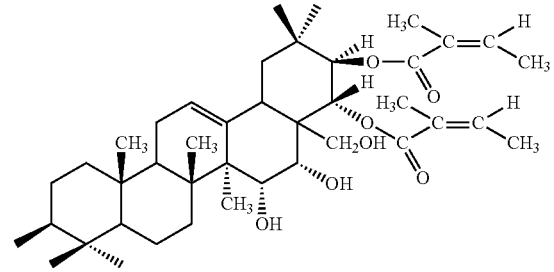

A method on its extraction: grinding the husk and fruit stem of *Xanthoceras Sobifolia* into particles, extracting the particles with solvents, filtrating, reclaiming the solvent and collecting the concentrated solution, passing the collection through macroporous resin, eluting it by solvent, reclaiming the solvent to get the enriched solution, drying the solution to form a brown solid which called total saponins; then dissolving the total saponins in water, extracting by normal butyl alcohol, having the extraction dried to obtain brown powder, chromatographing the powder resolved solution by silica gel column repeatedly, receipting the gradient elution with 100:(35~60) chloroform:methanol, reclaiming the eluted solution, refining and re-crystallize the left solution, will obtain the white raphide which is the invention compound—Xanthoceraside. It is verified that the compound can be used to make medicine to treat brain diseases and tumors, and to make health food to prevent and cure brain diseases and tumors.

18 Claims, 21 Drawing Sheets

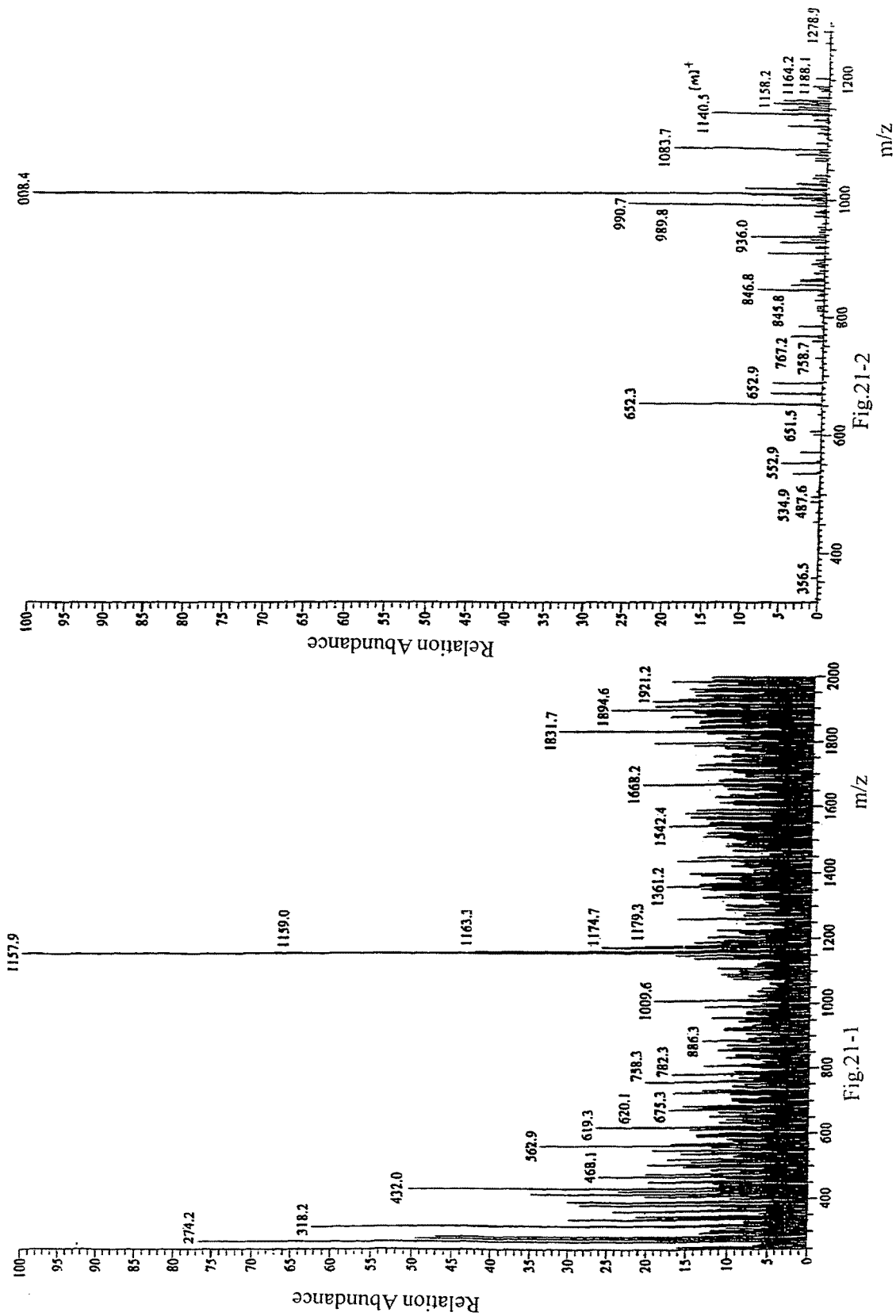

COMPOUND EXTRACTED FROM HUSK AND FRUIT STEM OF *XANTHOCERAS SOBIFOLIA* AND ITS EXTRACTING METHOD AND USE THEREOF

TECHNICAL FIELD

The present invention relates to the technology and method developed and used to discover the composition and application of an extracted compound from Husk and Fruit Stem of *Xanthoceras Sobifolia* (or *Xanthoceras Sobifolia* Bunge).

BACKGROUND ART

*Xanthoceras Sobifolia* Bunge, belonging to genus *Xanthoceras* family Sapindaceae, is a kind of woody oil-bearing plant endemic to China. There is only one species in the genus. The plant mainly distributes in Liaoning Province, Inner Mongolia Autonomous Region and Hexi corridor in Gansu Province in China. It has the drought resistant, cold hardy, barren land enduring, saline and alkali tolerant, and high anti-pest characteristics, also has easy regeneration, early fecundity and long-life properties. There are about 700,000 Mu (about 47,000 hectares) of it growing in the northern area of China for sand fixed forest.

*Xanthoceras Sobifolia*'s kernel contains oil up to 60%, which consisting of 14 unsaturated fatty acids. The oil is edible, tastes pleasant and can be used to treat enuresis on infant. So far, the husk and the fruit stem of *Xanthoceras Sobifolia* have been considered as abandoned resource and have not been developed and used to benefit human beings.

DISCLOSURE OF INVENTION

The aim of the present invention is to provide the compound from the husk and fruit stem of *Xanthoceras Sobifolia*, its extracted and refined methods, and its applications on medicine. This invention will not only have the trashed husk and fruit stem of *Xanthoceras Sobifolia* as a useful resource, but also develop a new medicine to treat brain diseases and tumors.

In order to realize the purposes above-mentioned, the technical procedure of the invention is as follows:

The present invention offers the compound from the husk and fruit stem of *Xanthoceras Sobifolia*, which is named as Xanthoceraside, classifying to triterpenoid saponins. Its chemical structure is as follows:

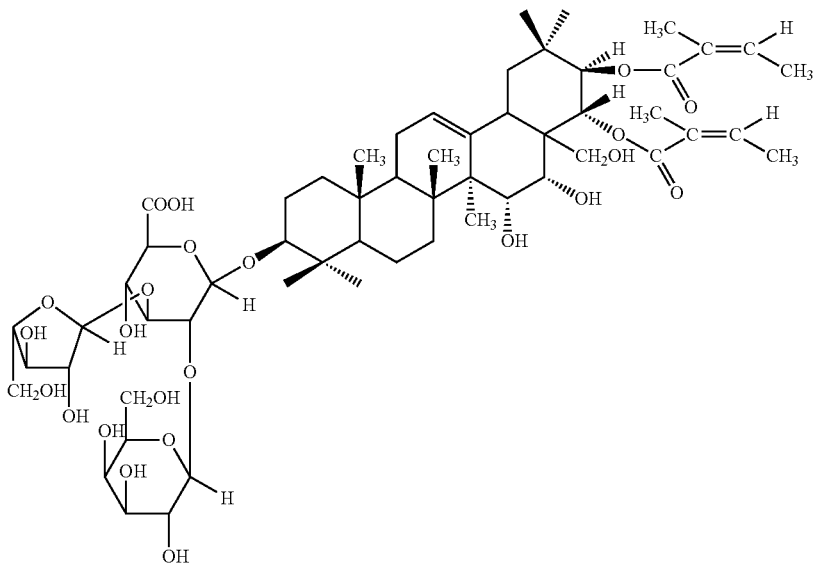

3-O-(α-L-arabinofuranosyl(1→3)-β-D-galactopyranosyl(1→2))-β-D-glucuronopyranosyl-21, 22-diangeloyl-$R_1$-barrigenol The compound is a kind of white raphide, melting point between 267~268° C. When measuring it with spectrophotometer at 254 nm wavelength, the Cambridge (faint) red stain is emerged, and when dissolved into sulfuric acid solution it appears transparent purple. Its Molish reaction is positive.

The extracting method: Grinding the husk and/or fruit stem of *Xanthoceras Sobifolia* into particles, immersing the particles by solvents for a predefined time, filtrating the solution, evaporating and condensing the solvents to enrich the filtrate, the concentrated solution is then passed through microporous resin. Eluting the solution with solvents, reclaiming solvents from the collection, the residual, after distilled and dried to form solid brown, is the effective compositions called total saponins. Dissolving the total saponins in water, extracting it by normal butyl alcohol, drying it, a brown powder is obtained. For several times of chromatographing the dissolved powder with silica gel and eluting the solution stepwise with 100:35~60 chloroform/methanol to refine it, a white acerose crystal is obtained which is the new compound called Xanthoceraside.

The solvent according to the process above includes water, methanol, propanol, butyl alcohol and/or acetone. Methanol, propanol, butyl alcohol or acetone is taken 35%~85% of total volume.

The extracting procedure above adopts a method of interval stirring, i.e. stirring the solvent for 1~5 minutes at the interval of 10~20 minutes. The extracting procedure will take 1~3 hours at the temperature of 60~100° C.

Application of the compound: This compound can be used as a medicine to treat brain diseases and tumors, and/or as a functional health food to prevent and treat brain diseases and tumors.

Advantages of this Invention:

The invention has extracted a brand new compound, Xanthoceraside, from the husk and fruit stem of *Xanthoceras Sobifolia*. By indexing CA-CS and SCIFINDER, this compound, as a new member of triterpenoid saponins, has not been found and reported by anyone else. According to the test results on animals, this compound showed positive effect on improving brain functions, i.e. amending the ability of cognition, abating brain anoxemia. From the treatment test on cancer cell in vitro, the compound showed great inhibiting effect on cancers cells. Therefore, this invention not only digs values of husk and fruit stem of *Xanthoceras Sobifolia*, turning it into precious resource, but also develops a new medicine and a functional health food to treat brain diseases and tumors. All its applications are very promising.

BRIEF DESCRIPTION OF THE DRAWINGS

FIG. 21-1: MS spectrum of Xanthoceraside.

FIG. 21-2: MS$^2$ spectrum of Xanthoceraside.

DESCRIPTION OF THE INVENTION IN DETAIL

Example 1

Figure 1:
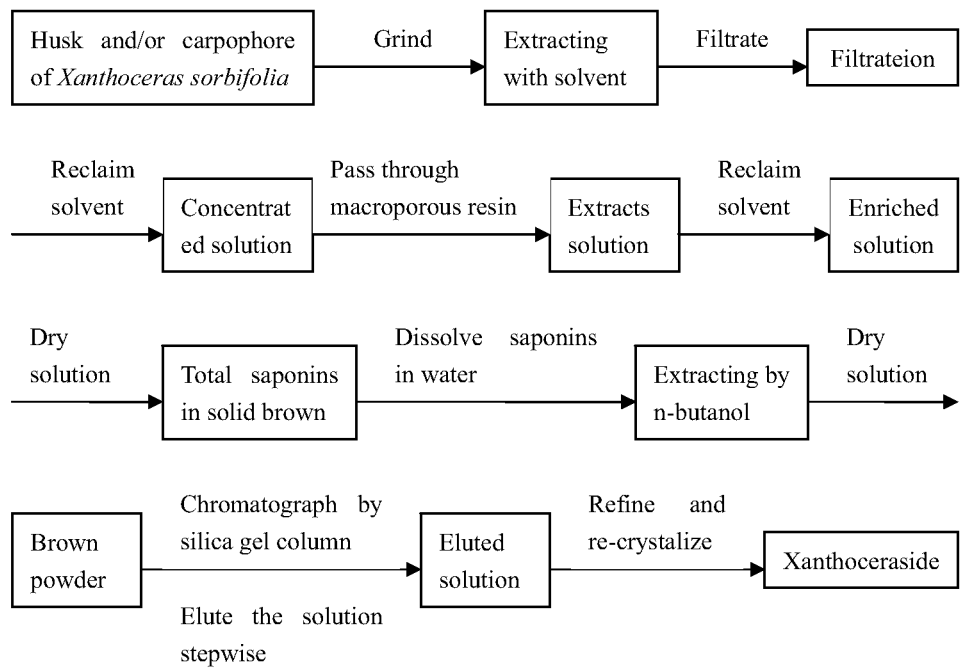
FIG. 1: Procedure to extract the new compound from the husk and fruit stem of *Xanthoceras Sobifolia*.
Figure 2:
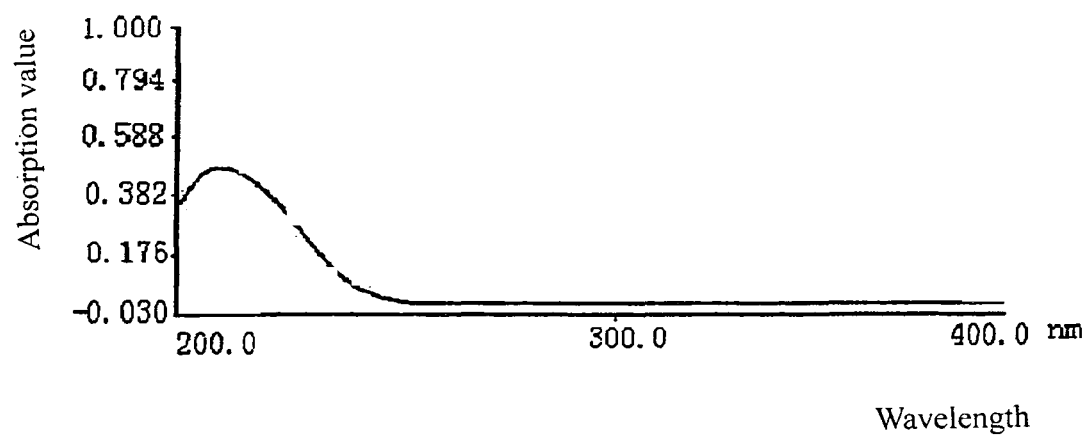
FIG. 2: Ultraviolet spectrogram of Xanthoceraside (wavelength: 211.6 nm, absorption value: 0.4554, peak height: 0.1920).
Figure 3:
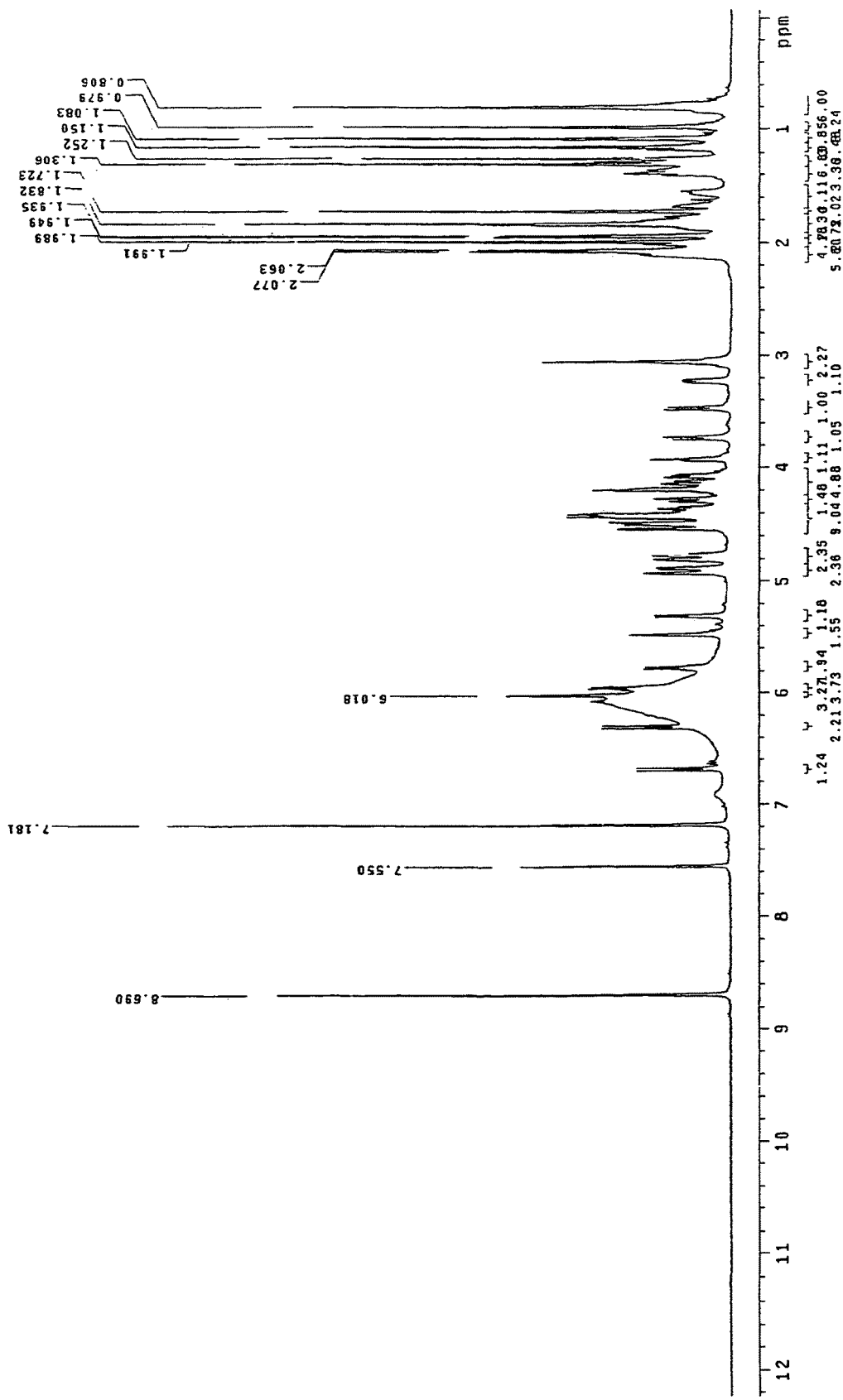
FIG. 3: $^1$H NMR spectrum of Xanthoceraside. Test condition: solvent: pyd, Temperature: 25.0° C./298.1K, INOVA-500"BMU500", Relax delay: 2.000 sec, Pulse: 47.0 degrees, Acq time: 1.892 sec, width: 7998.4 Hz, 32 repetitions, FT size: 65536, Total time: 2 min 4 sec. (BUM-500-$^1$H, δ 0~12 ppm).
Figure 4:
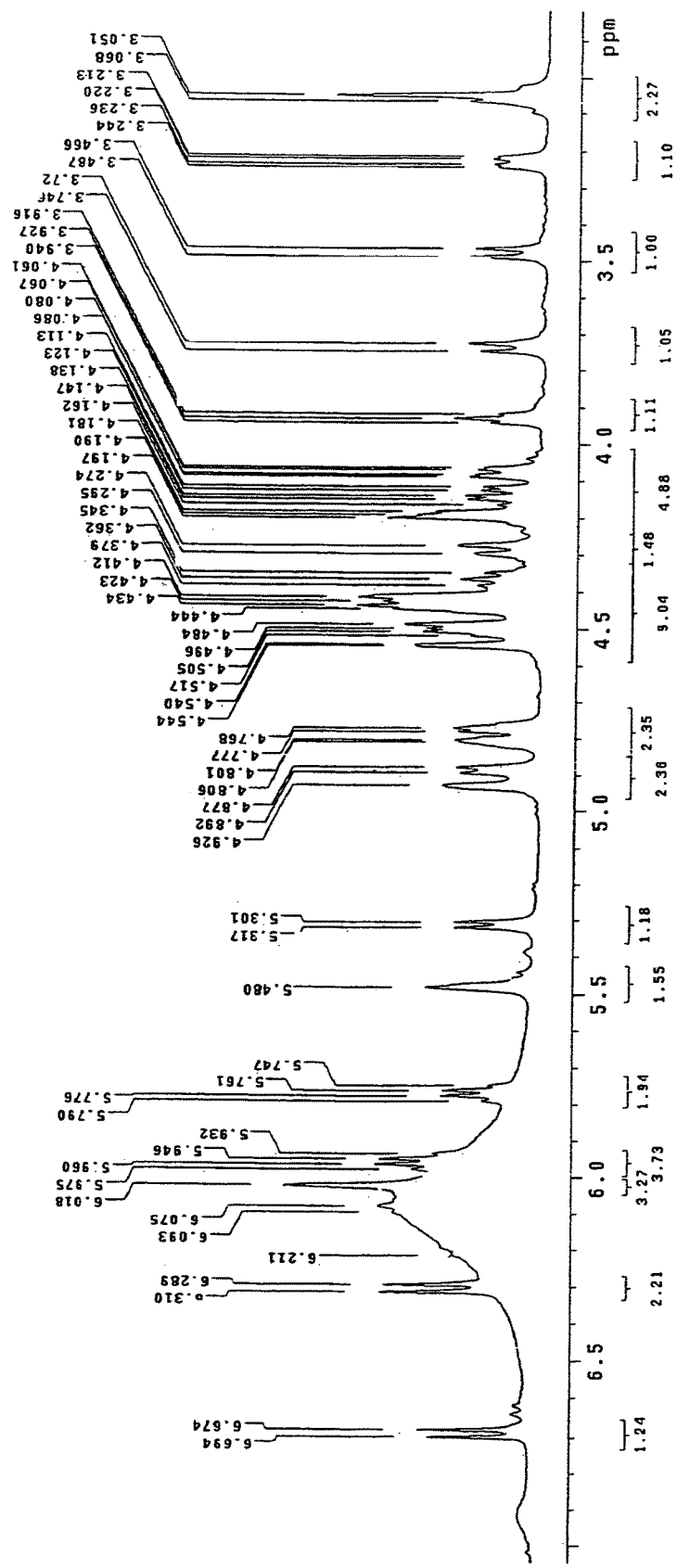
FIG. 4: Enlarged $^1$H NMR spectrum of Xanthoceraside (Part I). Test condition: solvent: pyd, Temperature: 25.0° C./298.1K, INOVA-500"BMU500", Relax delay: 2.000 sec, Pulse: 47.0 degrees, Acq time: 1.892 sec, width: 7998.4 Hz, 32 repetitions, FT size: 65536, Total time: 2 min 4 sec. (BUM-500-$^1$H, δ 3.0~7.0 ppm).
Figure 5:
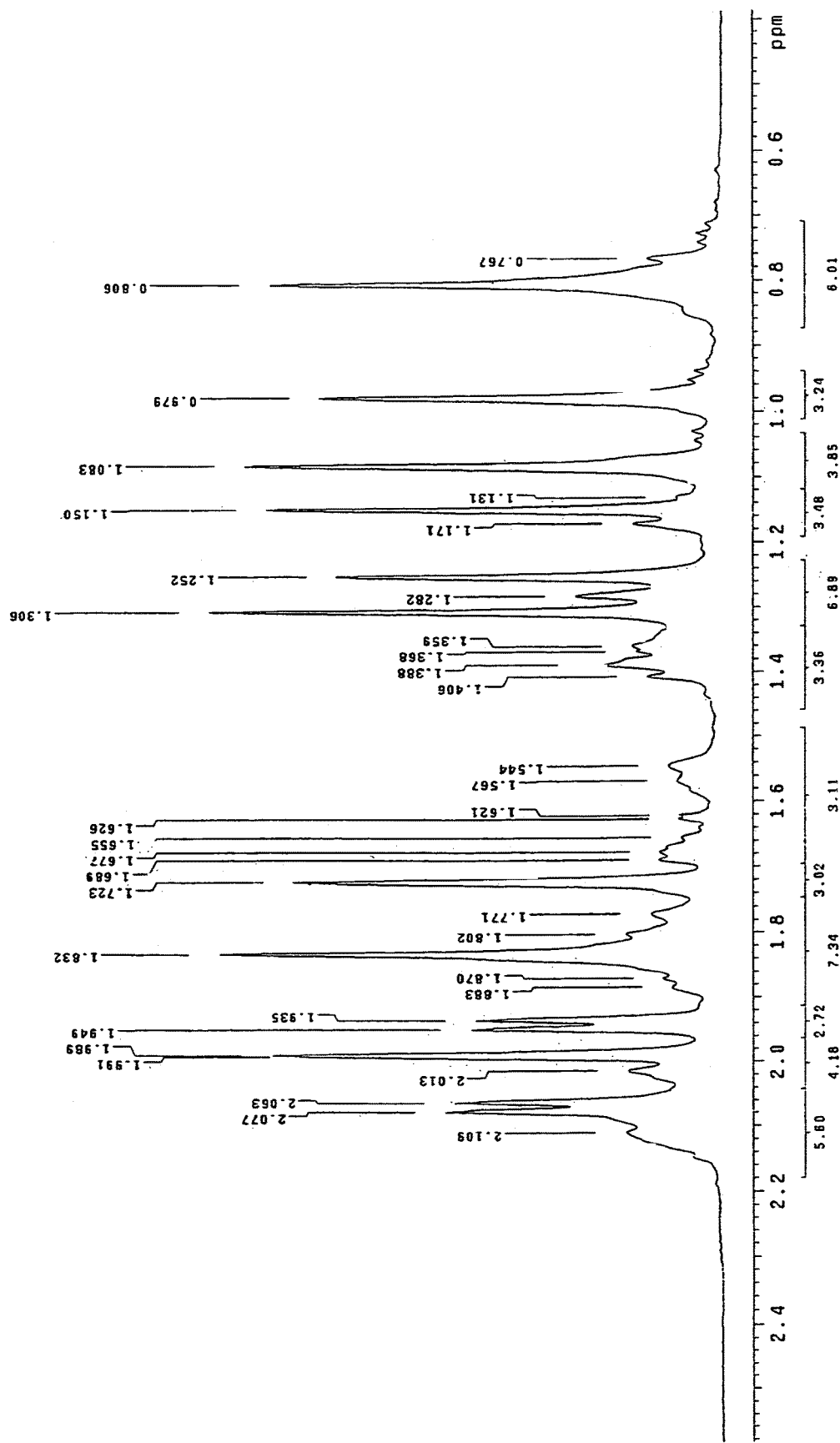
FIG. 5: Enlarged $^1$H NMR spectrum of Xanthoceraside (Part II). Test condition: solvent: pyd, Temperature: 25.0° C./298.1K, INOVA-500"BMU500", Relax delay: 2.000 sec, Pulse: 47.0 degrees, Acq time: 1.892 sec, width: 7998.4 Hz, 32 repetitions, FT size: 65536, Total time: 2 min 4 sec. (BUM-500-$^1$H, δ 0.4~2.4 ppm).
Figure 6:
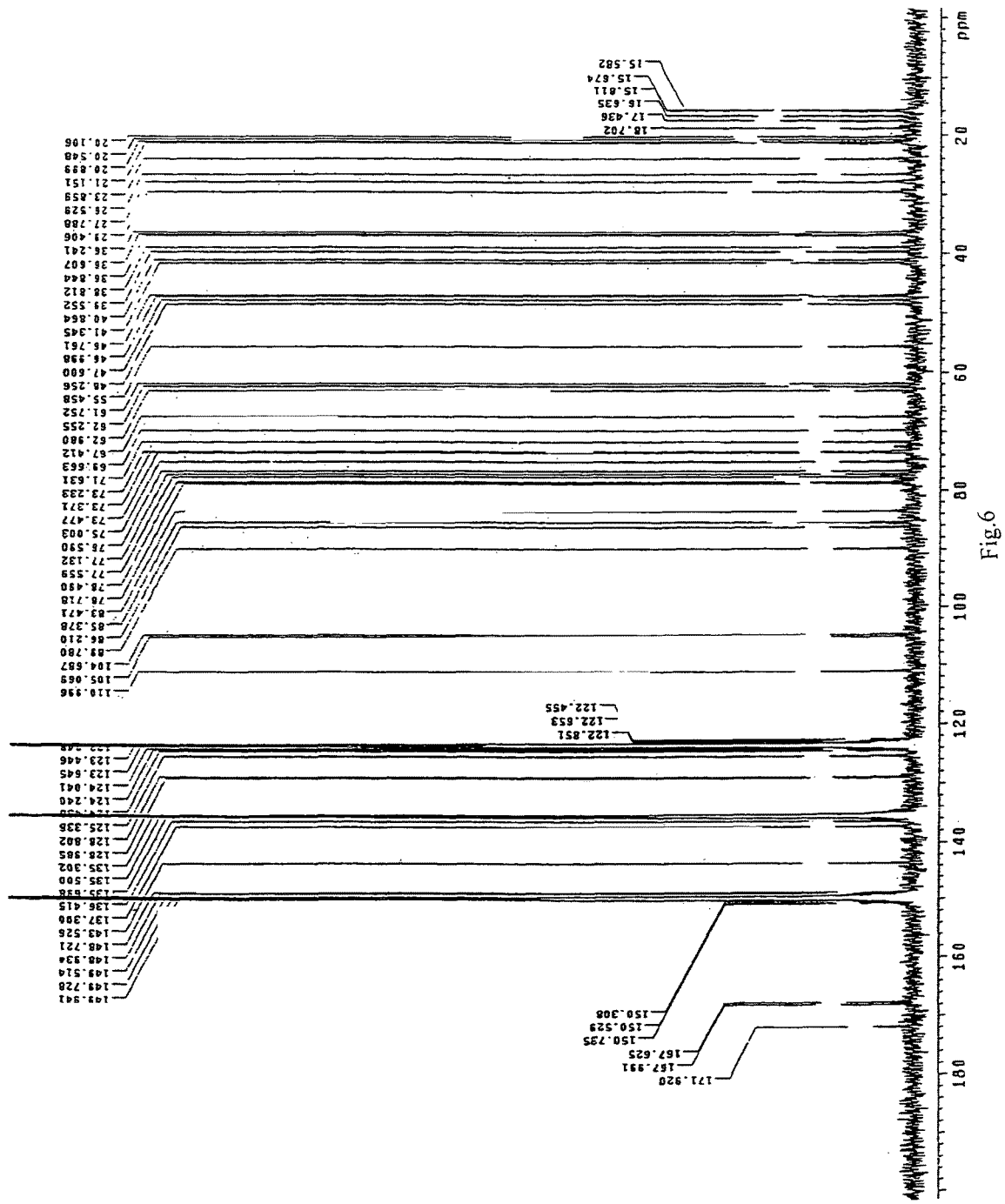
FIG. 6: $^{13}$C NMR spectrum of Xanthoceraside. Test condition: solvent: pyd, Temperature: 25.0° C./298.1K, INOVA-500"BMU500", Relax delay: 1.000 sec, Pulse: 30.0 degrees, Acq time: 0.600 sec, Width: 31421.8 Hz, 8896 repetitions, Line broadening: 3.5 Hz, FT size: 65536, Total time: 7 hr 19 min 20 sec. (BUM-500-$^{13}$C, δ 10~180 ppm).
Figure 7:
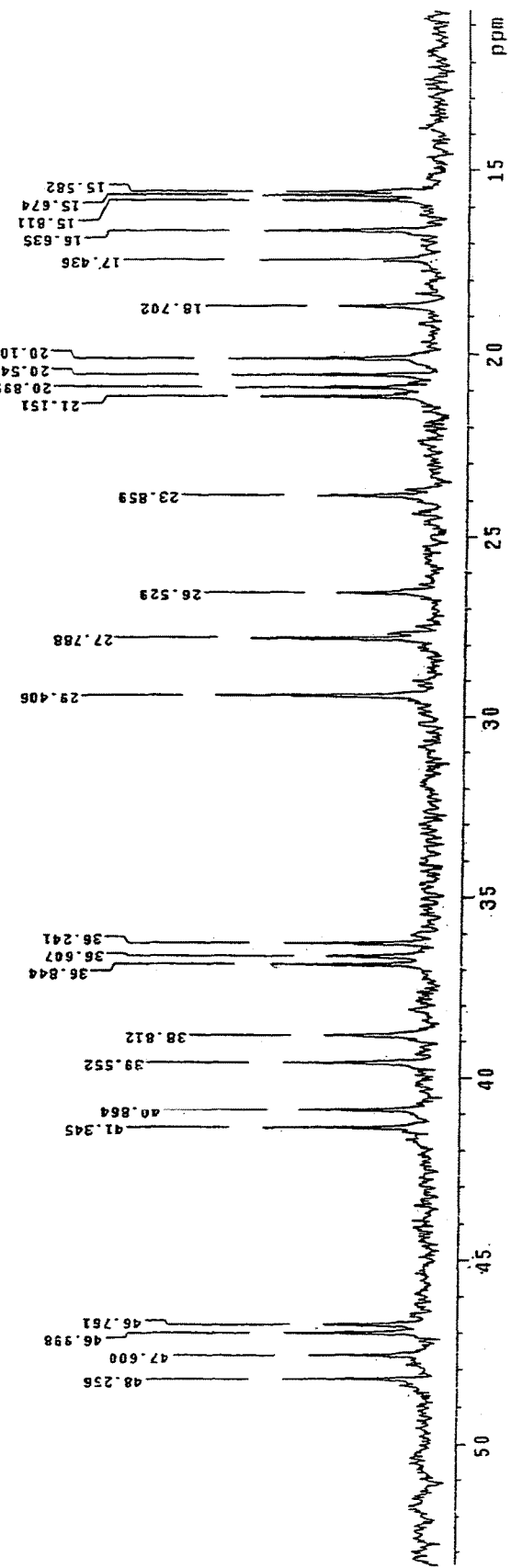
FIG. 7: Enlarged $^{13}$C NMR spectrum of Xanthoceraside (Part I). Test condition: solvent: pyd, Temperature: 25.0° C./298.1K, INOVA-500"BMU500", Relax delay: 1.000 sec, Pulse: 30.0 degrees, Acq time: 0.600 sec, width: 31421.8 Hz, 8896 repetitions, Line broadening: 3.5 Hz, FT size: 65536, Total time: 7 hr 19 min 20 sec. (BUM-500-$^{13}$C, δ 10~50 ppm).
Figure 8:
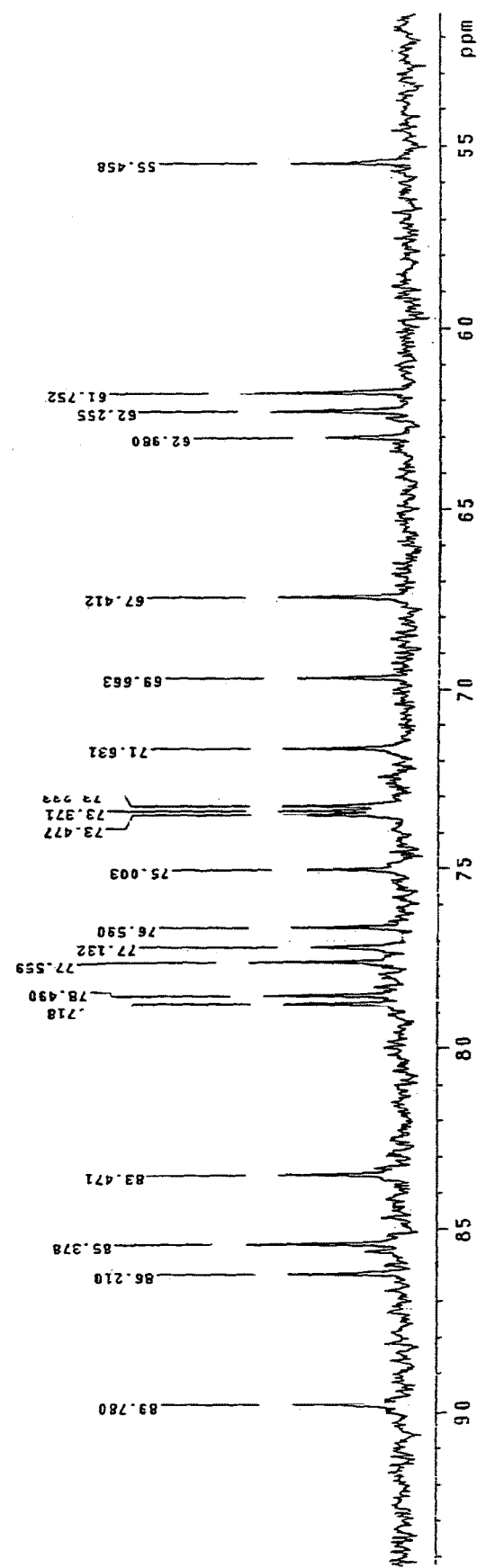
FIG. 8: Enlarged $^{13}$C NMR spectrum of Xanthoceraside (Part II). Test condition: solvent: pyd, Temperature: 25.0° C./298.1K, INOVA-500"BMU500", Relax delay: 1.000 sec, Pulse: 30.0 degrees, Acq time: 0.600 sec, width: 31421.8 Hz, 8896 repetitions, Line broadening: 3.5 Hz, FT size: 65536, Total time: 7 hr 19 min 20 sec. (BUM-500-$^{13}$C, δ 51~94 ppm).
Figure 9:
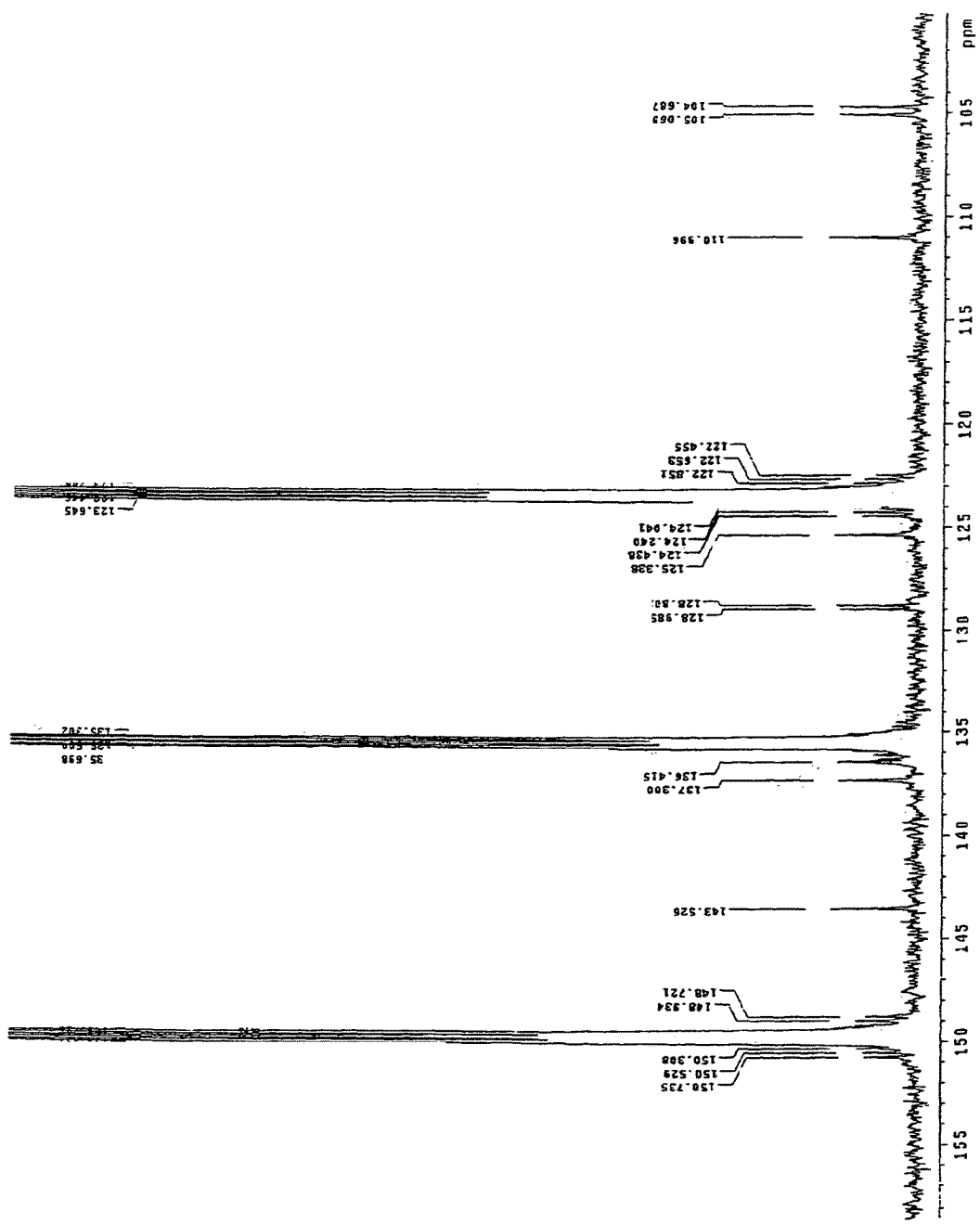
FIG. 9: $^{13}$C NMR spectrum of Xanthoceraside (Part III). Test condition: solvent: pyd, Temperature: 25.0° C./298.1K, INOVA-500"BMU500", Relax delay: 1.000 sec, Pulse: 30.0 degrees, Acq time: 0.600 sec, Width: 31421.8 Hz, 8896 repetitions, Line broadening: 3.5 Hz, FT size: 65536, Total time: 7 hr 19 min 20 sec. (BUM-500-$^{13}$C, δ 100~155 ppm).
Figure 10:
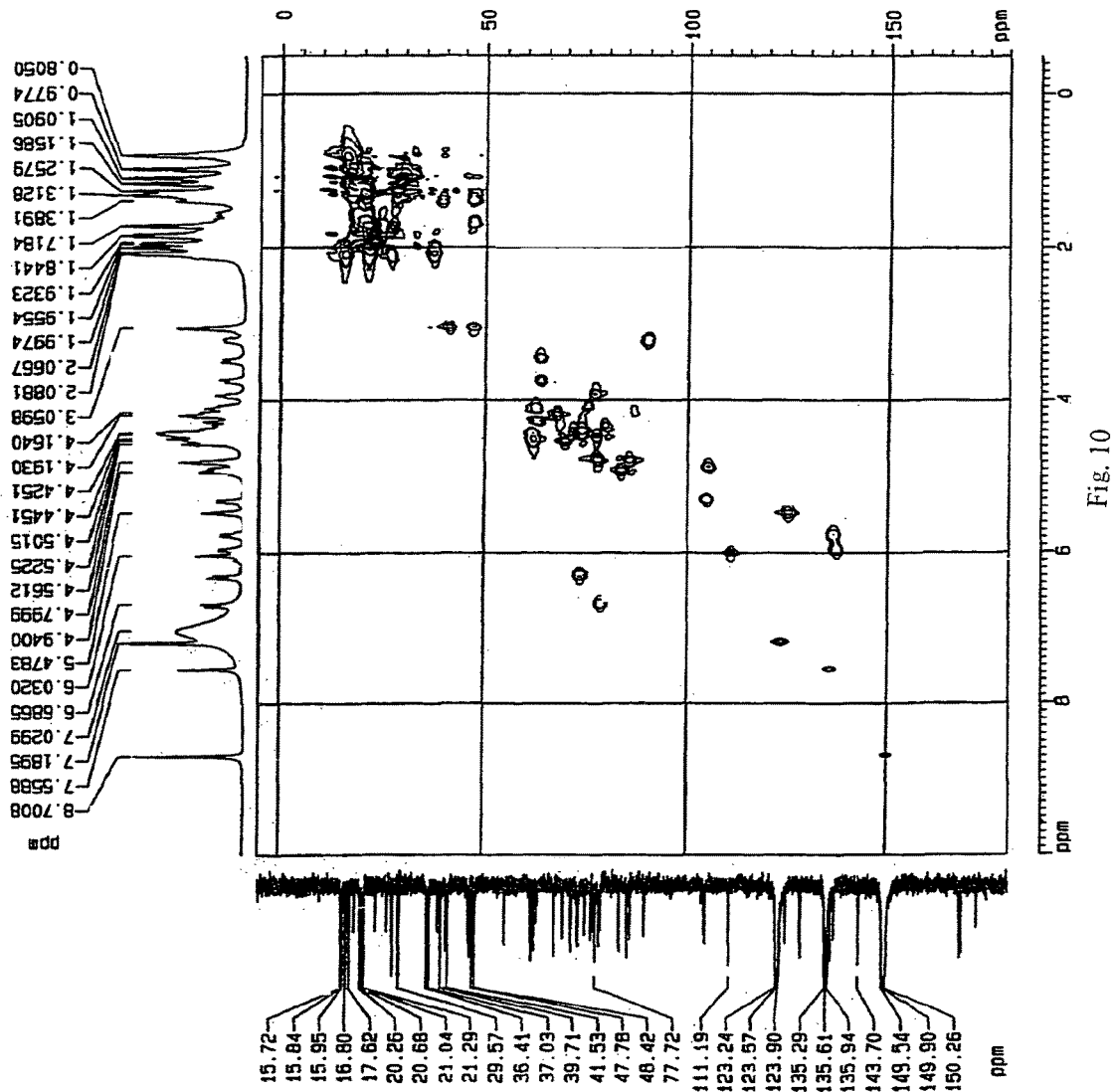
FIG. 10: $^1$H—$^{13}$C COSY of Xanthoceraside. Test condition: solvent: pyd, Burker-ARX-300, TE: 300K, D1: 1.00000000 sec, P1: 9.80 μsec, AQ: 0.1311220 sec, NS: 48, SWH: 3906.250 Hz, SI: 1024. (ARX-300, $^1$H-: δ 0~10 ppm, $^{13}$C—: δ 0~180 ppm).
Figure 11:
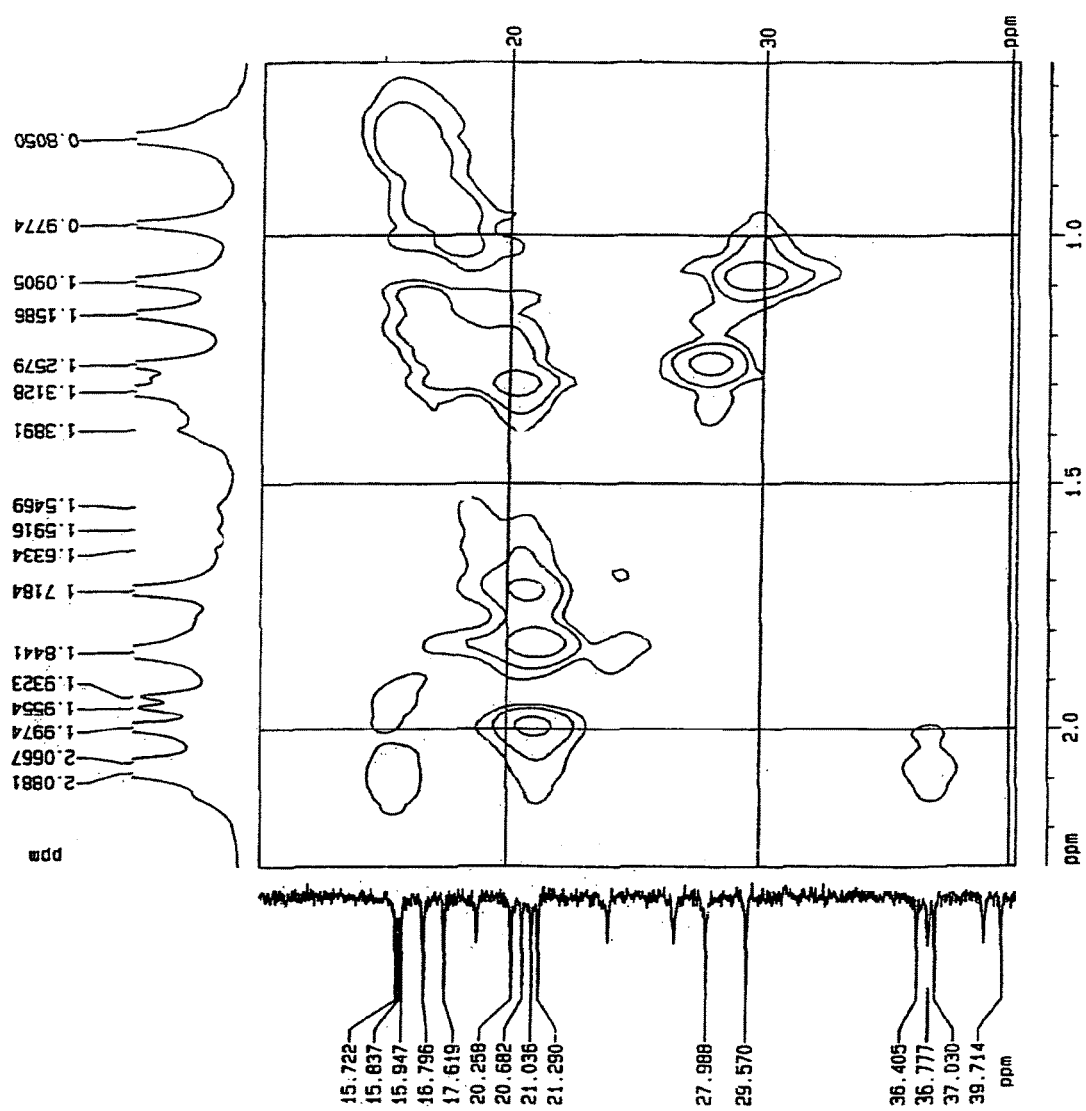
FIG. 11: Enlarged $^1$H—$^{13}$C COSY of Xanthoceraside (Part I). Test condition: solvent: pyd, Burker-ARX-300, TE: 300K, D1: 1.00000000 sec, P1: 9.80 μsec, AQ: 0.1311220 sec, NS: 48, SWH: 3906.250 Hz, SI: 1024. (ARX-300, $^1$H—: δ 0.7~2.3 ppm, $^{13}$C—: δ 10~40 ppm).
Figure 12:
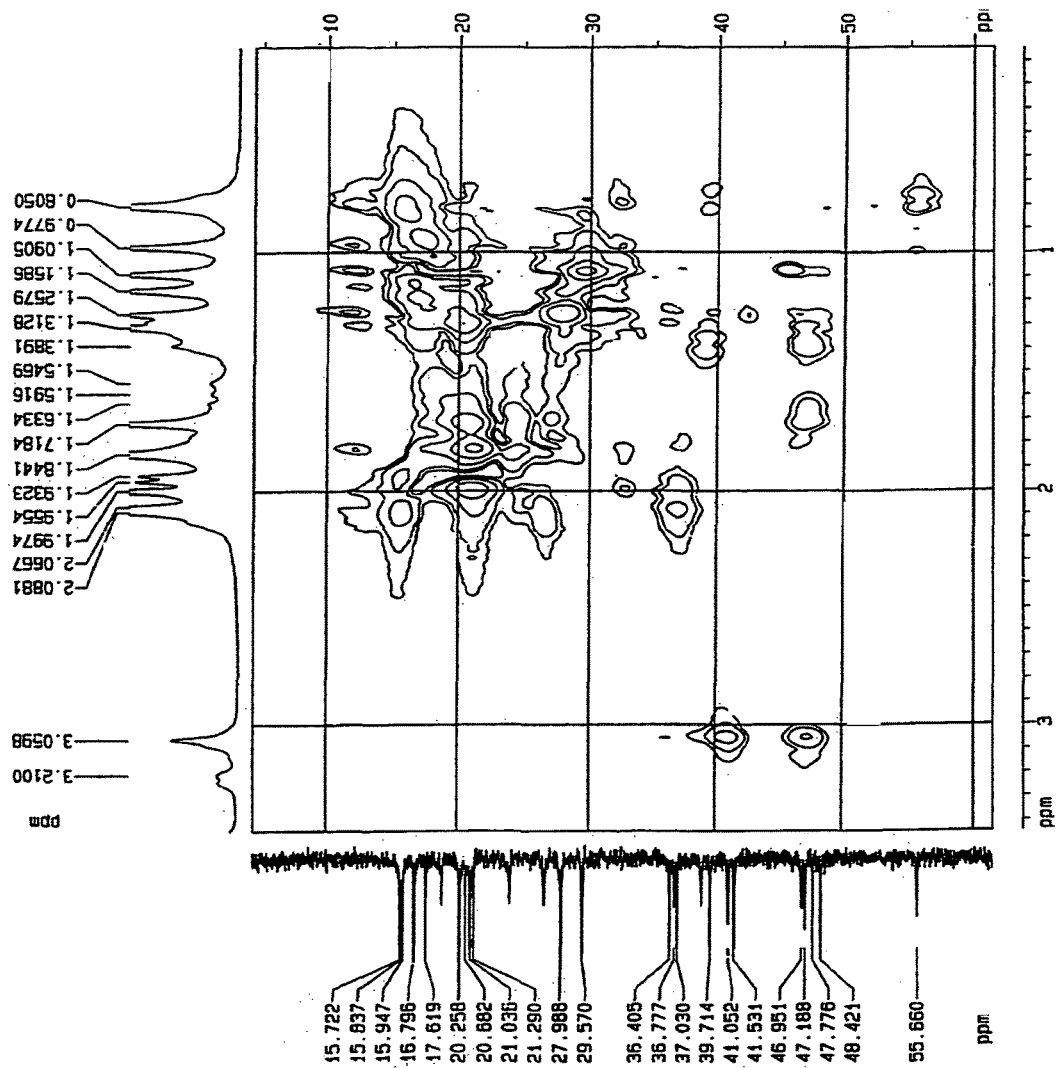
FIG. 12: Enlarged $^1$H—$^{13}$C COSY of Xanthoceraside (Part II). Test condition: solvent: pyd, Burker-ARX-300, TE: 300K, D1: 1.00000000 sec, P1: 9.80 μsec, AQ: 0.1311220 sec, NS: 48, SWH: 3906.250 Hz, SI: 1024. (ARX-300, $^1$H—: δ 0.2~3.4 ppm, $^{13}$C-: δ 5~60 ppm).
Figure 13:
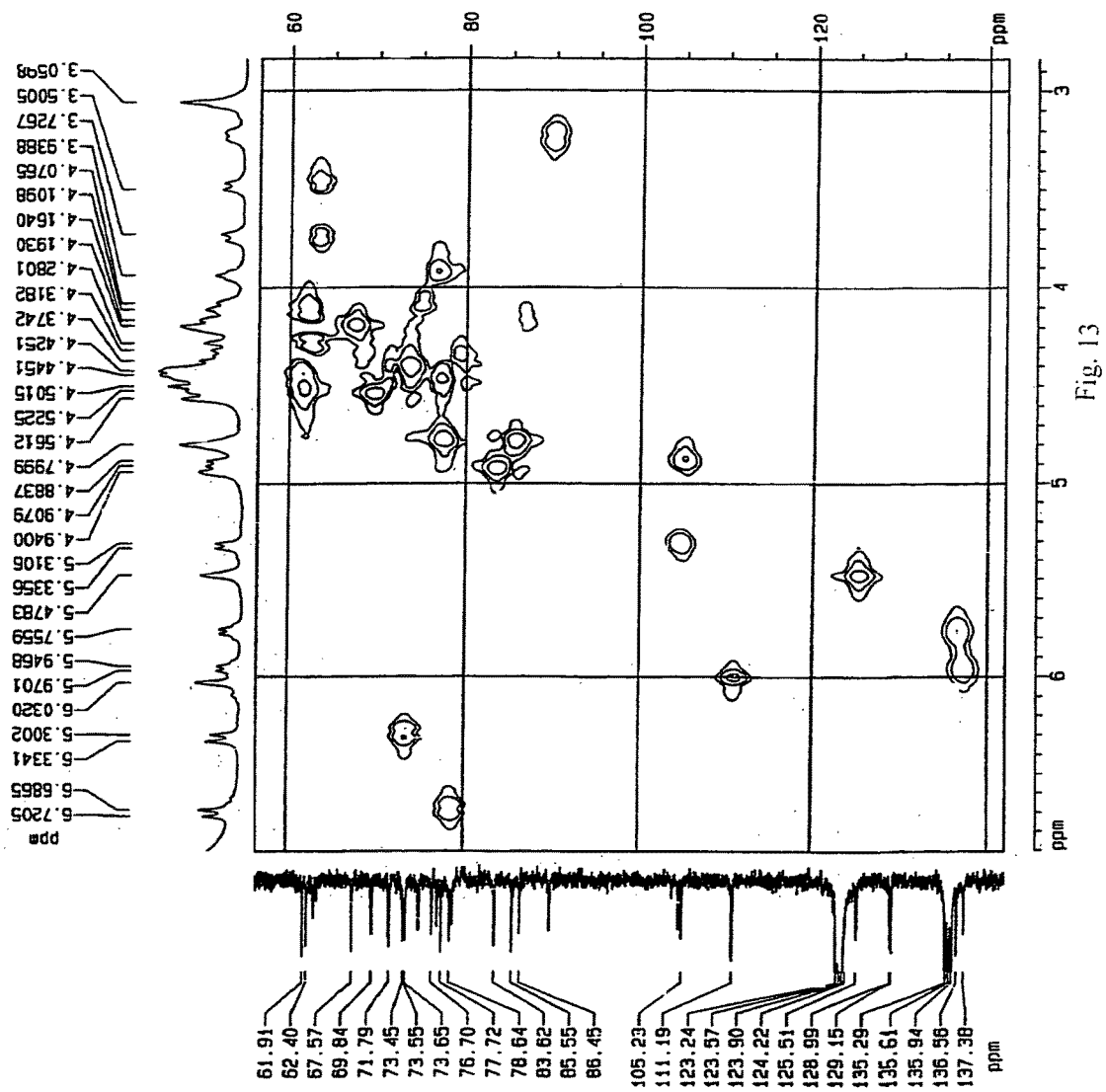
FIG. 13: Enlarged $^{13}$C—$^1$H COSY of Xanthoceraside (Part III). Test condition: solvent: pyd, Burker-ARX-300, TE: 300K, D1: 1.00000000 sec, P1: 9.80, sec, AQ: 0.1311220 sec, NS: 48, SWH: 3906.250 Hz, SI: 1024. (ARX-300, $^1$H—: δ 3~7 ppm, $^{13}$C—: δ 60~140 ppm).
Figure 14:
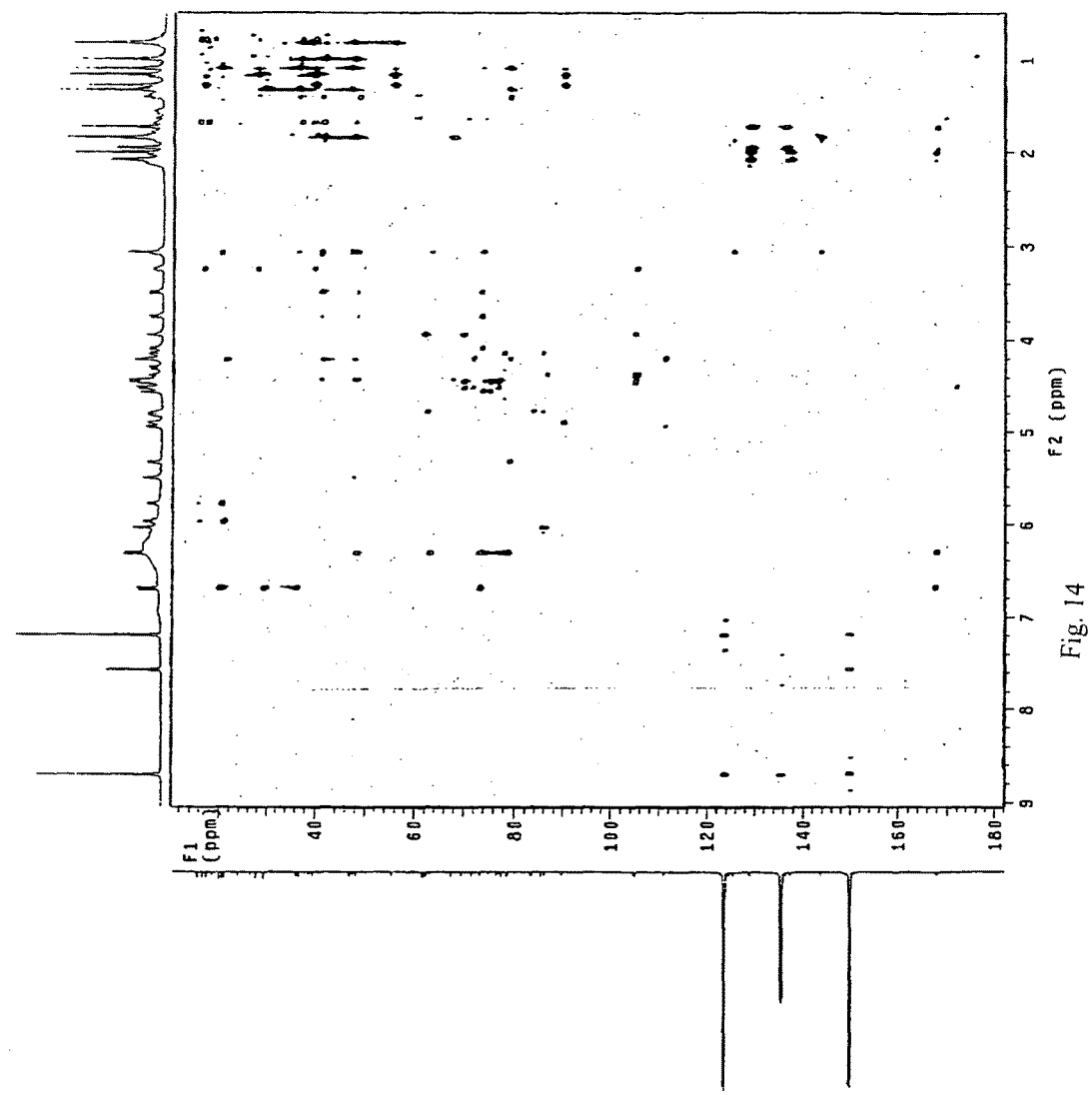
FIG. 14: $^{13}$C—$^1$H HMBC of Xanthoceraside. Test condition: solvent: pyd, Temperature: 25.0° C./298.1K, I NOVA-500 "BMU500", Relax delay: 1.000 sec, Acq time: 0.206 sec, Width: 4973.9 Hz, 2D Width: 30165.9 Hz, FT size: 2048×2048, Total time: 2 hr 18 min 44 sec. (BMU-500, $^1$H—:F$_2$0.6~9 ppm, $^{13}$C—:F$_1$10~180 ppm).
Figure 15:
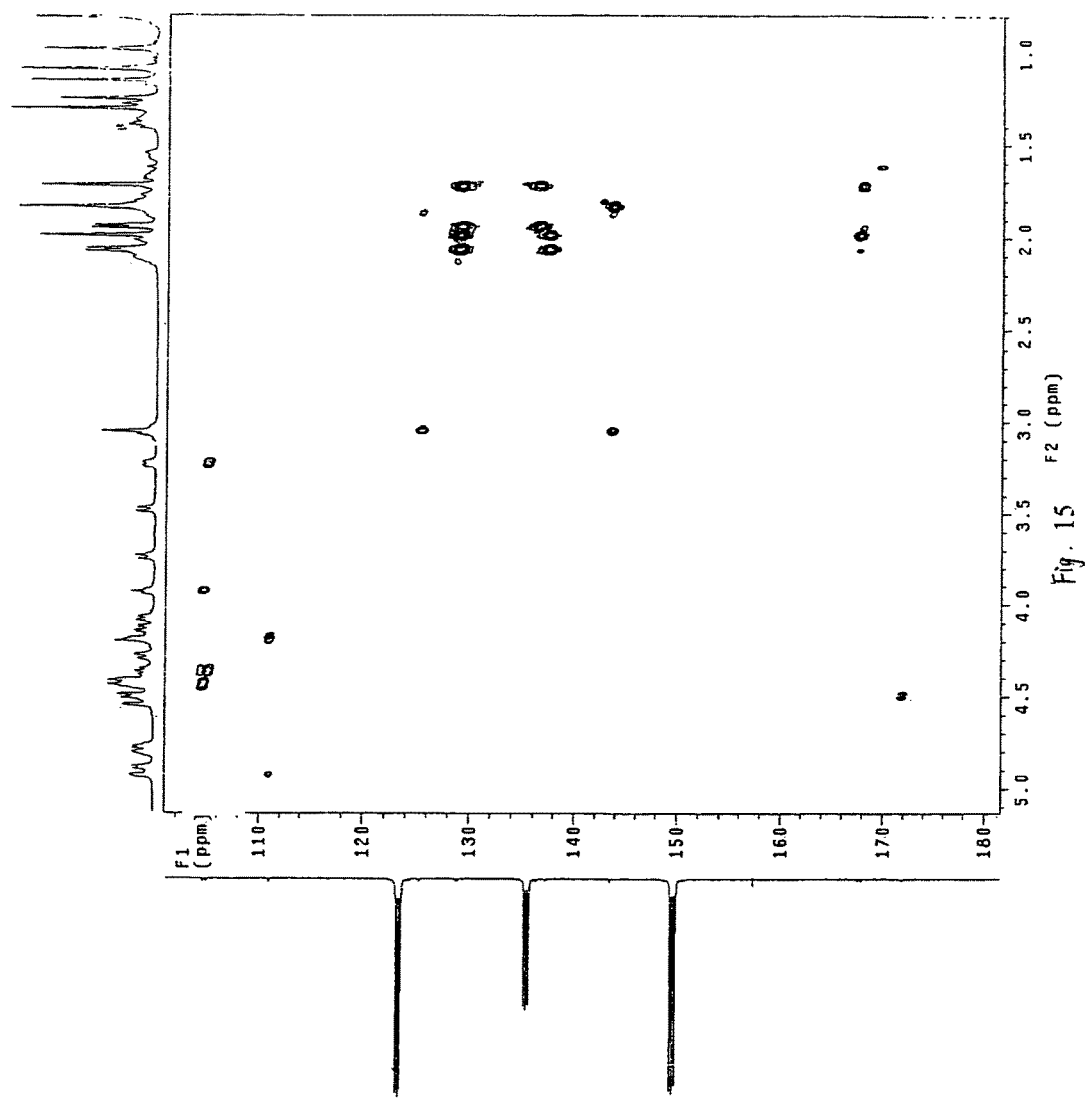
FIG. 15: Enlarged $^{13}$C—$^1$H HMBC of Xanthoceraside (Part I). Test condition: solvent: pyd, Temperature: 25.0° C./298.1K, I NOVA-500 "BMU500", Relax delay: 1.000 sec, Acq time: 0.206 sec, Width: 4973.9 Hz, 2D Width: 30165.9 Hz, FT size: 2048×2048, Total time: 2 hr 18 min 44 sec. (BMU-500, $^1$H—: F$_2$0.8~5.1 ppm, $^{13}$C—: F$_1$100~180 ppm).
Figure 16:
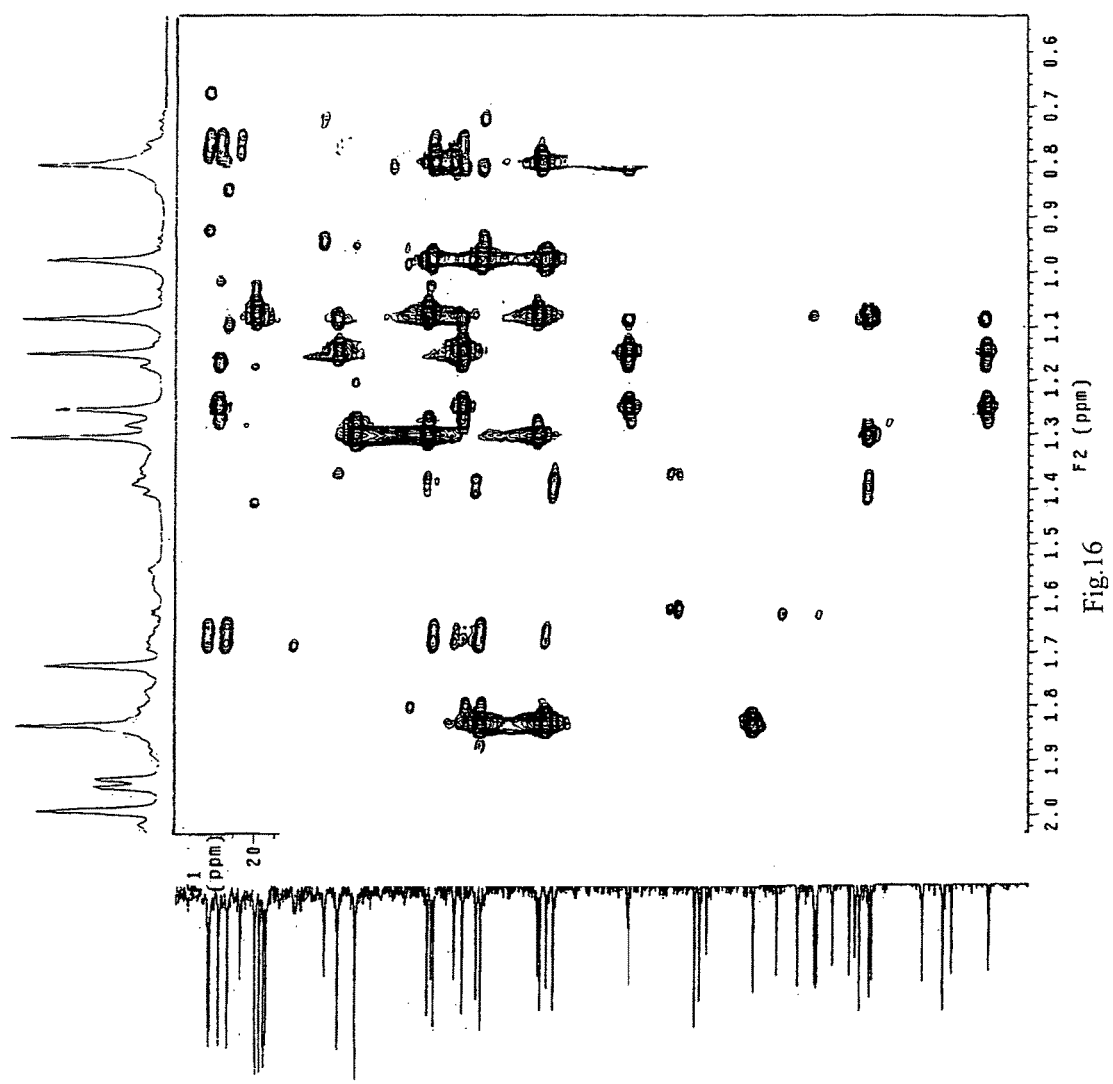
FIG. 16: Enlarged $^{13}$C—$^1$H HMBC of Xanthoceraside (Part II). Test condition: solvent: pyd, Temperature: 25.0° C./298.1K, INOVA-500 "BMU500", Relax delay: 1.000 sec, Acq time: 0.206 sec, Width: 4973.9 Hz, 2D Width: 30165.9 Hz, FT size: 2048×2048, Total time: 2 hr 18 min 44 sec. (BMU-500, $^1$H—: F$_2$ 0.54~2 ppm, $^{13}$C—F$_1$15~90 ppm).
Figure 17:
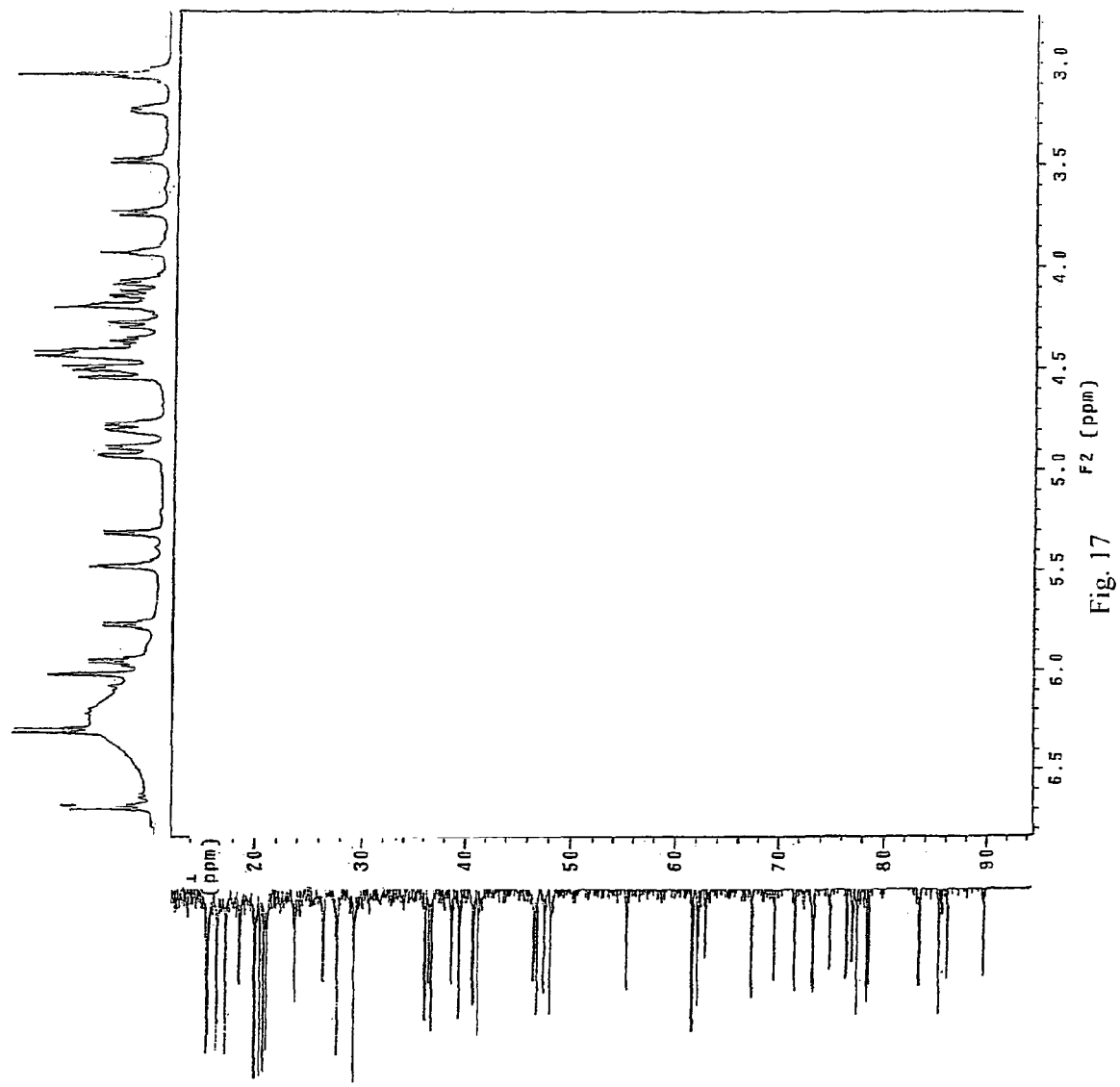
FIG. 17: Enlarged $^{13}$C—$^1$H HMBC of Xanthoceraside (Part III). Test condition: solvent: pyd, Temperature: 25.0° C./298.1K, INOVA-500 "BMU500", Relax delay: 1.000 sec, Acq time: 0.206 sec, Width: 4973.9 Hz, 2D Width: 30165.9 Hz, FT size: 2048×2048, Total time: 2 hr 18 min 44 sec. (BMU-500, $^1$H—: F$_2$2.8~6.8 ppm, $^{13}$C—: F$_1$10~94 ppm).
Figure 18:
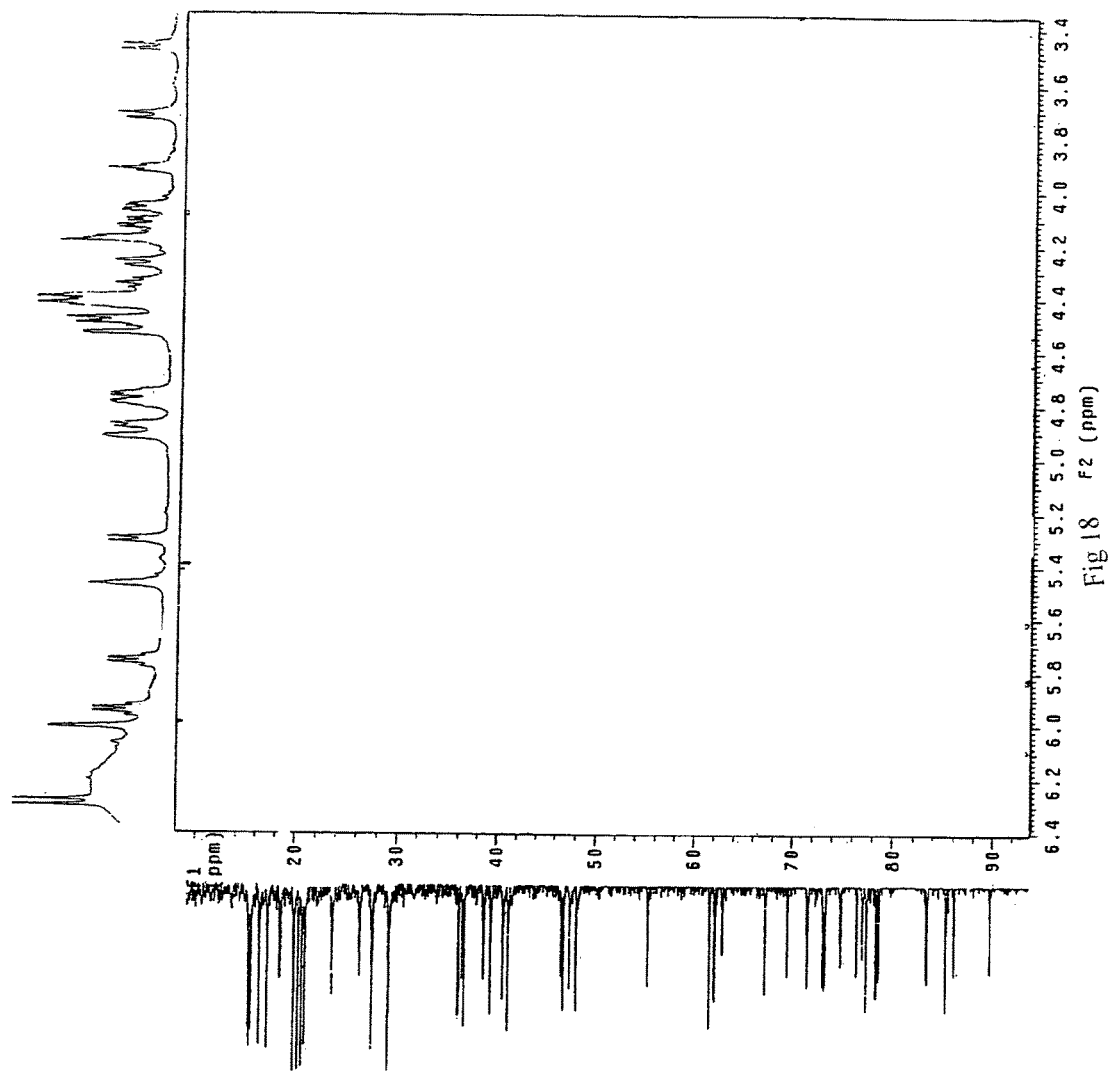
FIG. 18: Enlarged $^{13}$C—$^1$H HMBC of Xanthoceraside (Part IV). Test condition: solvent: pyd, Temperature: 25.0° C./298.1K, INOVA-500 "BMU500", Relax delay: 1.000 sec, Acq time: 0.206 sec, Width: 4973.9 Hz, 2D Width: 30165.9 Hz, FT size: 2048×2048, Total time: 2 hr 18 min 44 sec. (BMU-500, $^1$H—: F$_2$3.4~6.4 ppm, $^{13}$C—: F$_1$10~94 ppm).
Figure 19:
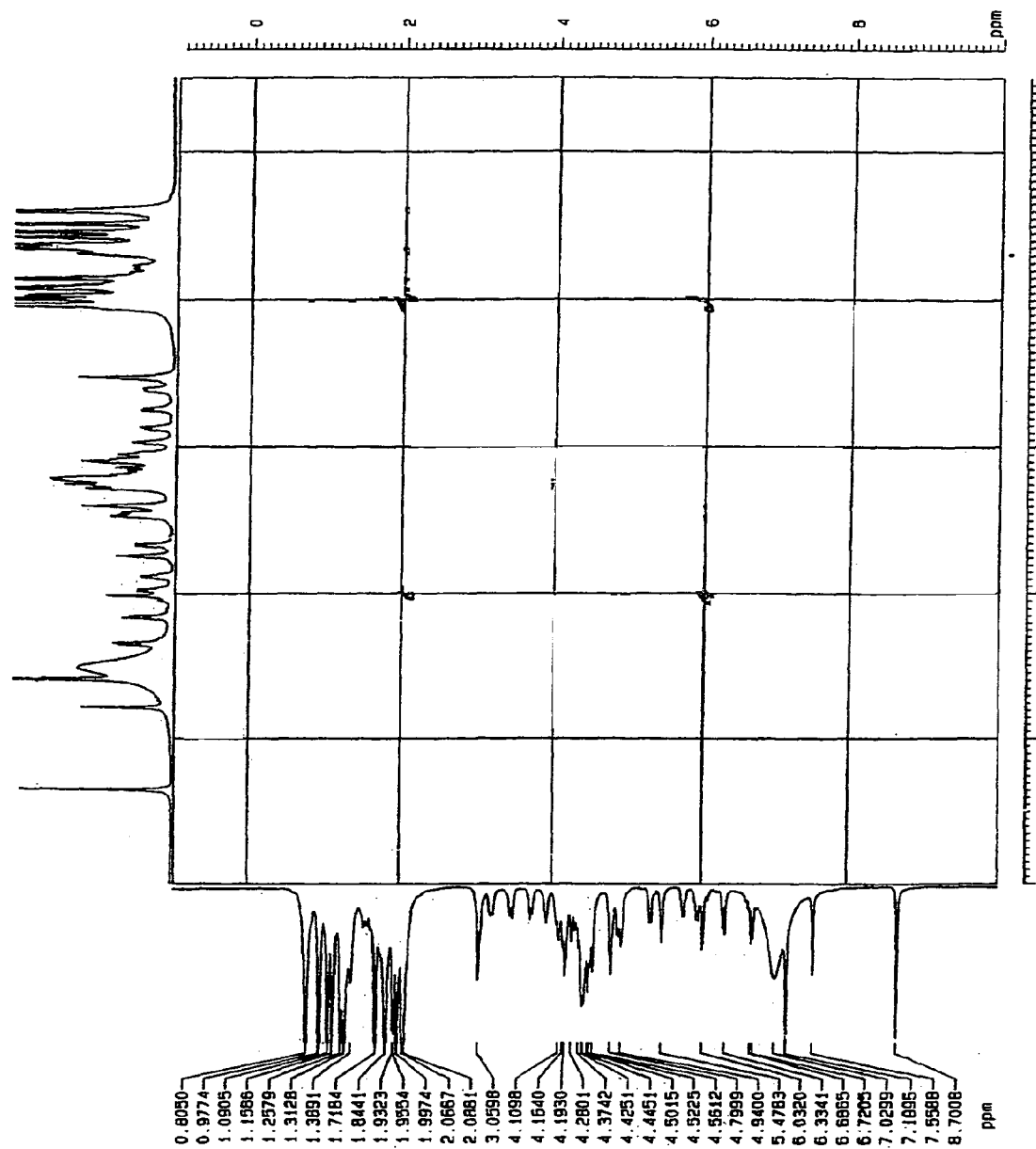
FIG. 19: $^1$H—$^1$H COSY of Xanthoceraside. Test condition: solvent: pyd, BRUKER-ARS-300, TE: 300K, D1:1.50000000 sec, P1: 9.80 μsec, AQ: 0.1311220 sec, NS: 48, SWH: 3906.250 Hz, SI: 512. (ARX-300, δ 0~10 ppm).
Figure 20:
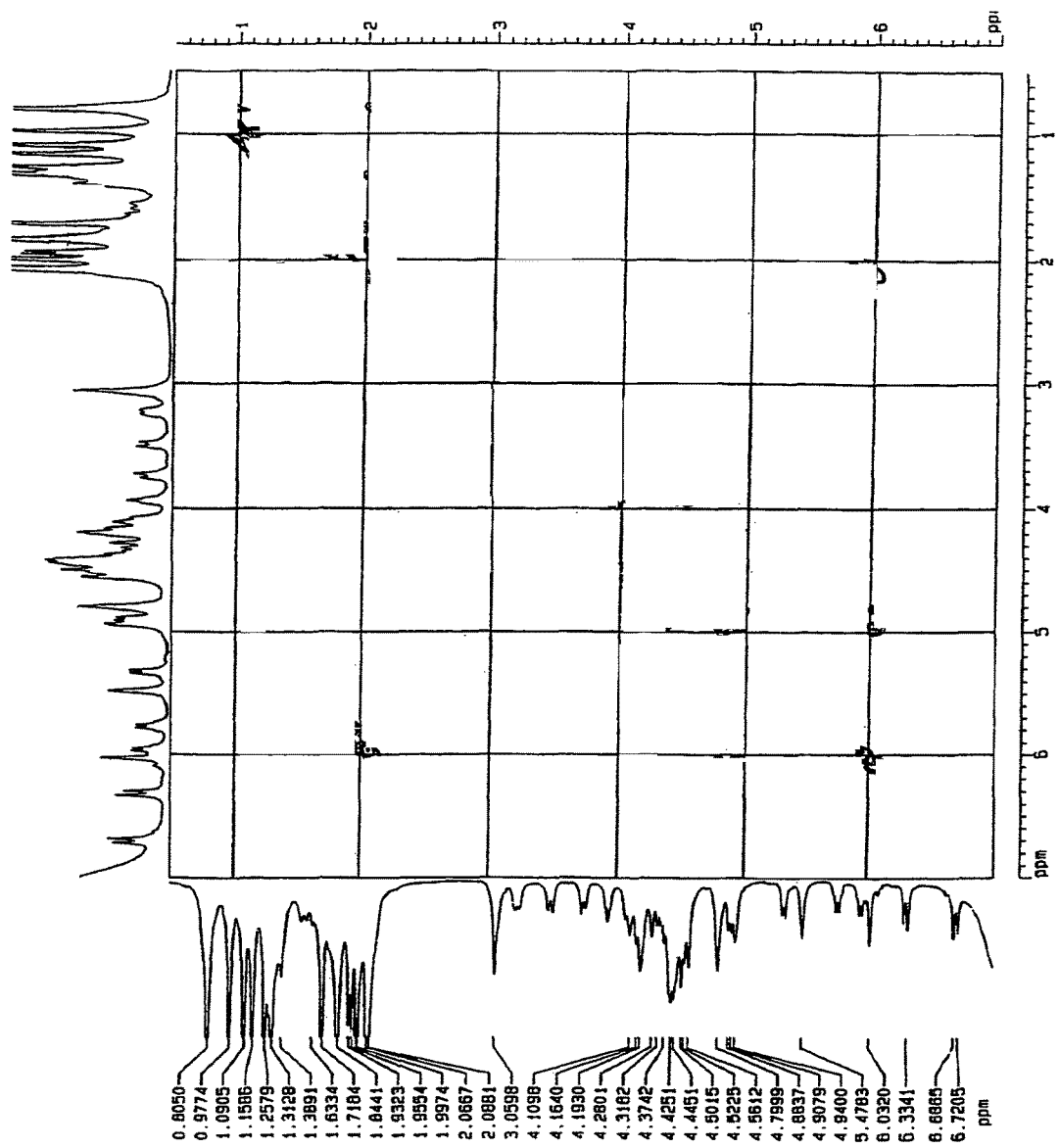
FIG. 20: Enlarged $^1$H—$^1$H COSY of Xanthoceraside. Test condition: solvent: pyd, BRUKER-ARS-300, TE: 300K, D1:1.50000000 sec, P1: 9.80 μsec, AQ: 0.1311220 sec, NS: 48, SWH: 3906.250 Hz, SI: 512. (ARX-300, δ 0.5~7 ppm).

Take 2,000 g husk of *Xanthoceras Sobifolia*, as shown in FIG. 1, grind it to particles the size of 30 meshes, extract it by using 35% (v/v) alcohol in 10 times the husk volume for 3 hours at temperature of 60° C. During extraction, stir the solvent for 1 minute every other 10 minutes, filtrate the extracting solution, reclaim alcohol and collect the residual. Elute the collection by using 35% alcohol through macroporous resin Model 101, enrich the effective composition, remove impurity, reclaim again the solvent, dry the residual, then the brown solid remained which is total saponins. Have the total saponins dissolved in water, extract it by using normal butyl alcohol, reclaim normal butyl alcohol, dry the left solution, then brown powder obtained. Subject the obtained aqueous extracts repeatedly to column chromatography over silica gel, elute it stepwise with 100:(35~60) of chloroform:methanol, reclaim the eluted solution and re-crystallized, will yield 50 mg white raphide which is the invention compound, Xanthoceraside.

Xanthoceraside on Animal Test:

20 female and male mice weighted 18~23 g were selected and divided evenly into two groups. The treatment group was fed with total dose of Xanthoceraside at the ratio of 9 mg/kg mice weight, and the control group was fed with the same amount of normal saline. After 40 minutes, they were put into Y maze respectively for performance observation. The number of incorrect alternations for a mice were recorded before it made correct choices continuously for 10 times. If errors more than 30, cutting the value to 30. The results are as follows:

TABLE 1

The effects of Xanthoceraside on improving
the learning and memory ability of mice

| Treatment | Number of mice | Dose (mg/kg) | Error frequency (X ± SD) | p-value |
|---|---|---|---|---|
| Normal saline | 10 | same volume | 28.2 ± 4.4 | — |
| Xanthoceraside | 10 | 9 | 6.9 ± 2.3 | <0.01 |

The data indicated that the Error frequency by the mice who took Xanthoceraside was significantly less than those who took normal saline (p<0.01). This shows Xanthoceraside has the function of improving mice's memory and study ability.

Example 2

Take 2,000 g fruit stem of *Xanthoceras Sobifolia* and grind it, as shown in FIG. 1, extract it by using 85% (v/v) normal butyl alcohol in the 8 times volume of the fruit stem of *Xanthoceras Sobifolia* for 1 hour at temperature of 75° C. During extraction, stir the solution for 5 minutes every other 20 minutes, filtrate the extracting solution, reclaim normal butyl alcohol and collect the residual. Elute the collection by 85% normal butyl alcohol through macroporous resin Model 101, enrich the effective composition, remove impurity, reclaim again the solvent, dry the residual, then the brown solid remained which is total saponins. Have the total saponins dissolved in water, extract it by using normal butyl alcohol, reclaim normal butyl alcohol, and dry the left solution, then brown power obtained. Subject the obtained aqueous extracts repeatedly to column chromatography over silica gel, elute stepwise with 100:(35~60) of chloroform: methanol, reclaim the eluted solution and re-crystallized, will yield 45 mg white raphide which is the invention compound, Xanthoceraside.

Xanthoceraside on Animal Test:

Mice were trained based on the stochastic three arms Y maze test, to screen those who had less than 30 errors of alternation before they continuously made correct choices for 10 times. After relaxed for 24 hours, the selected ones were randomized into two groups and for all of them scopolamine was injected into celiac at the ratio of 2.0 mg/kg mice weight to cause their learning and memory impairment. After 15 minutes, the mice in the treatment group were given an injection of total dose of Xanthoceraside at ratio of 6 mg/kg mice weight, while those in the control group were given an injection of the same amount of normal saline. After 20 minutes, they were arranged respectively into Y maze and the number of incorrect alternations before they made correct choices continuously for 10 times. The result is shown as follows:

TABLE 2

The effects of Xanthoceraside on recovering the memory
retrieval impairment of mice induced by scopolamine

| Treatment | Number of mice | Dose (mg/kg) | Error frequency (X ± SD) | p-value |
|---|---|---|---|---|
| Normal saline | 8 | same volume | 17.9 ± 3.6 | — |
| Xanthoceraside | 8 | 6 | 4.0 ± 1.5 | <0.01 |

From the above table, it shows that Xanthoceraside has the function of recovering the memory retrieval impairment of mice induced by scopolamine.

Example 3

Take 1,000 g husk and 1,000 g fruit stem of *Xanthoceras Sobifolia* and grind them respectively, extract them by using 50% (v/v) alcohol in 10 times volume of the husk and fruit stem of *Xanthoceras Sobifolia* for 2 hours at temperature of 90° C. During extraction, stir the solution for 3 minutes every other 15 minute, filtrate the extracting solution, reclaim alcohol and collect the residual. Elute the collection by 50% alcohol through macroporous resin Model 101, enrich the effective composition, remove impurity, reclaim again the solvent, dry the residual, then the brown solid remained which is total saponins; Have the total saponins dissolved in water, extract it by using normal butyl alcohol, reclaim normal butyl alcohol, dry the left solution, then brown powder obtained; Subject the obtained aqueous extracts repeatedly to column chromatography over silica gel, elute it with 100:(35~60) of chloroform:methanol, reclaim the eluted solution and re-crystallized, will yield 50 mg white raphide which is the invention compound, Xanthoceraside.

The above obtained Xanthoceraside was for the test of regular static hypoxia tolerance in an isolated environment to observe the effect of Xanthoceraside on death time of animals.

The test consisted of two sections. Each section was divided into two groups: control and treatment. There were three measurements to calculate death time of the mice. Those in treatment group took oral dosing of 2 mg of Xanthoceraside twice a day for 6 days. The three parameters are:

The average death time of whole group (xt);
The super average death time (xp): based on the average death time of the control group (xc), calculate the death time (xp), which is greater than the control group (xc), and calculate the mean.
The delayed death time (xp-xc): the super average death time (xp) minus the control group (xc) and calculated the mean.

The test results are shown in Table 3.

TABLE 3

The effect of Xanthoceraside on mice's death times

| Indices | Control group | Treatment group | p-value |
| --- | --- | --- | --- |
| First section: | | | |
| xt (min) | 34.5 ± 8.89(30※) | 41.84 ± 15.35(30) | <0.025 |
| xp(min) | 41.42 ± 4.48(14) | 56.51 ± 14.59(17) | <0.05 |
| xp − xc(min) | 5.54 4 ± 46(14) | 14.59 ± 14.83(17) | <0.05 |
| Second section: | | | |
| xt (min) | 25.38 ± 4.24(40) | 31.55 ± 6.68(41) | <0.001 |
| xp(min) | 27.54 ± 2.87(24) | 33.40 ± 4.94(33) | <0.001 |
| xp − xc(min) | 2.64 ± 2.87(24) | 8.40 ± 4.94(33) | <0.001 |

※number of mice

According to the results from table 3, it has significant differences for all the three measurements of death time among the control and treatment groups in two sections. Since mice's death time in treatment is longer than the time in control group, it can be verified that Xanthoceraside has the function to increase the level of hypoxia tolerance.

The brain is excessively sensitive to hypoxia because brain is the first organ to be affected. Xanthoceraside strengthens the ability of hypoxia tolerance so that it extends the death time of mice.

Example 4

Take 2,000 g husk of *Xanthoceras Sobifolia* and grind it, as shows in FIG. 1, extract it by using boiling water in 15 times the husk volume for 3 hours. During extraction, stir the solvent for 2 minutes every other 10 minutes, filtrate the extracting solution and partition through macroporous resin Model 101, elute it by water, enrich the effective composition, remove impurity, vaporize to concentrate the extracts, separate the extracts from water with normal butyl alcohol, reclaim normal butyl alcohol, dry the solvent, then brown powder remained, chromatograph the dissolved powder repeatedly through silica gel column, elute it with 100: (35~60) of chloroform:methanol, reclaim the eluted solution and re-crystallized, then obtain 40 mg white raphide which is the invention compound, Xanthoceraside.

Also, Methanol, propanol or acetone can be used as the extracting solvent in the invention.

Example 5

Take Xanthoceraside derived from the example 3 to do a test on tumor cell in vitro. The methods and results are shown in Table 4.

TABLE 4

The anti-tumor activity assays of Xanthoceraside against six human tumor cell lines in vitro

| No. | Dyeing method (Tumor cell model) | Dose (μg/ml) | Observed indices | Testing effects | Result | $IC_{50}$ (μg/ml) |
| --- | --- | --- | --- | --- | --- | --- |
| 1 | MTT (HL-60 human leukemia) | 0.5 5.0 50.0 | Inhibition ratio (%) | 9.34 17.68 56.90 | + | 41.29 |
| 2 | SRB (PC-3MIE8 human prostate cancer) | 0.5 5.0 50.0 | Inhibition ratio (%) | −13.90 −7.63 92.03 | + | 40.98 |
| 3 | SRB (BGC-823 human gastric cancer) | 0.5 5.0 50.0 | Inhibition ratio (%) | −11.71 −5.92 92.45 | + | 40.24 |
| 4 | SRB (MDA-MB-435 human breast cancer) | 0.5 5.0 50.0 | Inhibition ratio (%) | −4.50 2.92 93.14 | + | 18.58 |
| 5 | SRB (Bel-7402 human liver cancer) | 0.5 5.0 50.0 | Inhibition ratio (%) | −9.78 −1.24 92.96 | + | 39.32 |
| 6 | SRB (Hela cervical cancer) | 0.5 5.0 50.0 | Inhibition ratio (%) | −12.72 −4.05 95.49 | + | 34.23 |

MTT: Tetrazolium salt(for dyeing cells), SRB: Sulforhodamine B(for dyeing cells).
$IC_{50}$: The inhibitory concentration of 50% cells.

From the above table; Xanthoceraside exhibits a significant effect on the inhibition of six kinds of human tumor cells in vitro. For breast cancer the $IC_{50}$ of 18.58 μg/ml of Xanthoceraside is found to have an anti-tumor activity. The other five, such as cervical carcinoma, liver cancer, gastric cancer, stomach cancer, prostate cancer and leukaemia are in turn with $IC_{50}$ of 34.23 μg/ml, 39.32 μg/ml, 40.24 μg/ml, 40.98 μg/ml and 41.92 μg/ml, respectively. Therefore, Xanthoceraside shows the better inhibition effect on tumor cell at low density. With further research, the new medicine may be developed on tumors.

The compound, Xanthoceraside, derived in example 1, 2, 3, and 4, is analyzed to label the data and identify the structure based on the chemical method and the spectral method, the later including UV, ID-NMR, 2D-DMR, EI-MS and ESI-MS, etc. According to the data from UV, ESI-MS, $^1$H-NMR, $^{13}$C-NMR, HMQC, HMBC, TOCSY (the detailed information was showed in FIG. 2~21), and refer to following documents: [1] Chen Y J, Takeda t, Ogihara Y. Studies on the constituents of *Xanthoceras sorbifolia* Bunge. III. Minor prosapogenins from the fruits of *Xanthoceras sorbifolia* Bunge, [J]. Chem. Pharm. Bull., 1985, 33(1): 127-134; [2] Yoshikawa M, Harada E, Matsuda H, et al. Elatosides A and B, potent inhibitors of ethanol absorption in rats from the bark of Aralia elata Seem.: The structure-activity relationships of oleanolic acid oligoglycosid [J]. Chem. Pharm. Bull., 1993, 41(11): 2069-2071. [3] Yoshikawa M, Harada E, Murakami T, et al. Camelliasaponins B1, B2, C1, and C2, new type inhibitors of ethanol absorption in rats from the seeds of Camellia japonica L. [J]. Chem. Pharm. Bull., 1994, 42(3): 742-744, the structure of the compound is 3-O-(α-L-arabiofuranosyl(1→3)-β-D-galactopyranosyl(1→2))-β-D-glucuronopyranosyl-21,22-diangeloyl-R1-barrigenol. Its chemical structure is:

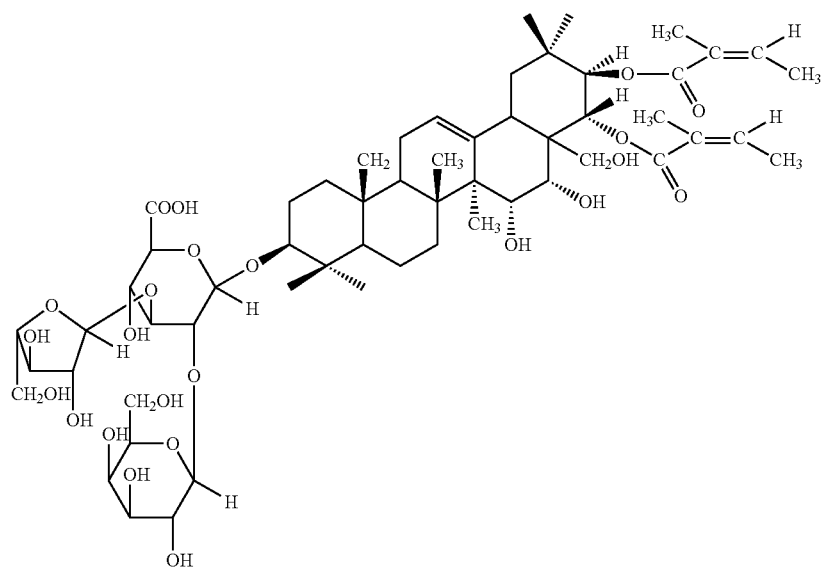

The detailed data of the compound obtained by the chemical method and the spectrum method are listed in Table 5.

TABLE 5

NMR results of Xanthoceraside

| No | $^{13}$C-NMR | $^1$H-NMR |
|---|---|---|
| Aglycone moiety | | |
| 1 | 39.7 | |
| 2 | 26.7 | |
| 3 | 89.9 | 3.21(1H, m) |
| 4 | 39.0 | |
| 5 | 55.7 | |
| 6 | 18.9 | |
| 7 | 36.4 | |
| 8 | 41.1 | |
| 9 | 47.2 | |
| 10 | 37.0 | |
| 11 | 24.0 | |
| 12 | 125.5 | 5.48(1H, brs) |
| 13 | 143.7 | |
| 14 | 47.8 | |
| 15 | 67.6 | |
| 16 | 73.4 | |
| 17 | 48.4 | |
| 18 | 41.5 | |
| 19 | 47.0 | |
| 20 | 36.8 | |
| 21 | 78.6 | 6.70(1H, d, J = 10.2 Hz) |
| 22 | 73.6 | 6.32(1H, d, J = 10.2 Hz) |
| 23 | 28.0 | 1.26(3H, s) |
| 24 | 16.8 | 1.16(3H, s) |
| 25 | 15.8 | 0.81(3H, s) |
| 26 | 17.6 | 0.98(3H, s) |
| 27 | 21.3 | 1.84(3H, s) |
| 28 | 63.2 | 3.73, 3.50(1H, d, J = 10.2 Hz) |
| 29 | 29.6 | 1.09(3H, s) |
| 30 | 20.3 | 1.31(3H, s) |
| Sugar moiety 3-o-glucuronopyranosyl moiety | | |
| 1' | 105.2 | 4.89(1H, d, J = 10.2 Hz) |
| 2' | 78.9 | |
| 3' | 86.4 | |
| 4' | 71.7 | |
| 5' | 77.3 | |
| 6' | 172.0 | |
| 2'-O-β-D-galactopyranosyl moiety | | |
| 1 | 104.9 | 5.32(1H, d, J = 7.5 Hz) |
| 2 | 73.5 | |
| 3 | 75.2 | |
| 4 | 69.8 | |
| 5 | 76.7 | |
| 6 | 61.9 | |
| 3'-O-α-L-arabinofuranosyl moiety | | |
| 1 | 111.2 | 6.03(1H, brs) |
| 2 | 83.6 | |
| 3 | 77.7 | |
| 4 | 85.5 | |
| 5 | 62.4 | |
| Angeloyl moiety | | |
| 1 | 167.8 | |
| 2 | 129.0 | |
| 3 | 137.4 | 5.96(1H, q, J = 7.0 Hz) |
| 4 | 15.9 | 2.09(3H, dq, J = 7.0 Hz) |
| 5 | 21.0 | 2.00(3H, m) |
| 1 | 168.2 | |
| 2 | 129.2 | |
| 3 | 136.6 | 5.76(1H, q. J = 6.6 Hz) |
| 4 | 15.7 | 1.93(3H, dq, J = 6.6 Hz) |
| 5 | 20.7 | 1.72(3H, m) |

To summarize the above description, the finding of the new compound increased the family member of triterpenoid saponins, which substantially enhanced the comprehensive utilization value of the husk and fruit stem of *Xanthoceras sobifolia*: It is very promising that new medicines will be developed to cure brain diseases and tumors.

What is claimed:

1. An isolated and purified compound having the following formula (I)

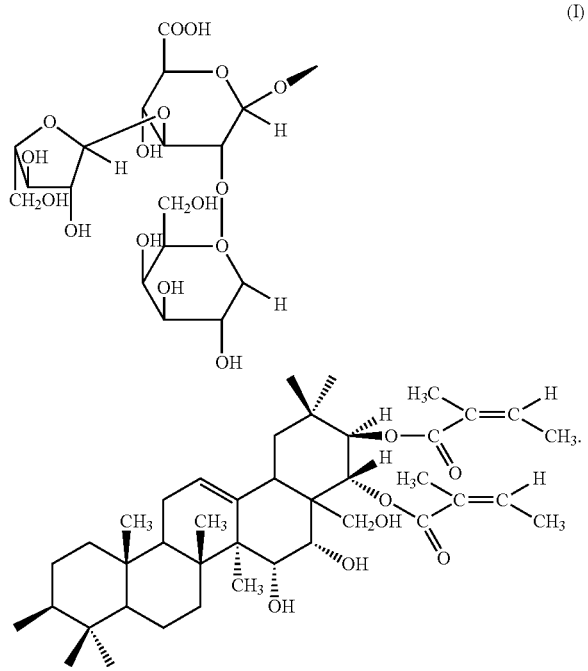

(I), wherein the compound is in a white raphide crystalline form.

2. The isolated and purified compound of claim 1, made by a process which comprises
   grinding a husk and fruit stem of *Xanthoceras Sobifolia* Bunge into particles,
   obtaining an extract by subjecting the particles to a mixture containing an organic solvent and an aqueous solution,
   filtering, evaporating, and condensing the extract to form a concentrated extract solution,
   subjecting the concentrated extract solution to column chromatography on macroporous resin to obtain a saponin extract solution;
   drying the saponin extract solution to obtain a saponin powder,
   dissolving the saponin powder in water to obtain a solution,
   subjecting the solution to silica gel chromatography,
   eluting with a 100:35-60 chloroform:methanol solution to obtain an eluate, and
   crystallizing the eluate to yield a white raphide.

3. The isolated and purified compound of claim 2, wherein the organic solvent is selected from the group consisting of methanol, ethanol, propanol, butanol, acetone, or a combination thereof.

4. The isolated and purified compound of claim 3, wherein the volume percentage of the organic solvent is about 35% to about 85%.

5. The isolated and purified compound of claim 2, wherein the step of obtaining the organic extract comprises stirring for about 1 to about 5 minutes every 10-20 minutes for about 1 to about 3 hours at a temperature of about 60° C. to about 100° C.

6. A method of treating a cancer in a subject which comprises administering to the subject having said cancer a therapeutically effective amount of the compound according to claim 1, wherein the cancer is breast cancer, cervical carcinoma, liver cancer, gastric cancer, stomach cancer, prostate cancer, or leukemia.

7. The method according to claim 6, wherein the compound is administered in the form of a food.

8. The isolated and purified compound of claim 4, wherein the volume of the organic solvent is not less than three times the weight of the particles.

9. The isolated and purified compound of claim 4, wherein the volume of the organic solvent is provided at a weight to volume ratio of the particles:solvent of 1:5-15.

10. The isolated and purified compound of claim 2, wherein the saponin extract is enriched by the macroporous resin chromatography.

11. A foodstuff or a medicine having the compound according to claim 1.

12. The method of claim 6, wherein the subject has breast cancer.

13. The method of claim 6, wherein the subject has cervical carcinoma.

14. The method of claim 6, wherein the subject has liver cancer.

15. The method of claim 6, wherein the subject has gastric cancer.

16. The method of claim 6, wherein the subject has stomach cancer.

17. The method of claim 6, wherein the subject has prostate cancer.

18. The method of claim 6, wherein the subject has leukemia.

* * * * *

UNITED STATES PATENT AND TRADEMARK OFFICE
CERTIFICATE OF CORRECTION

PATENT NO. : 9,884,884 B2  
APPLICATION NO. : 11/631637  
DATED : February 6, 2018  
INVENTOR(S) : Baizhen Yang, Songjiang Wang and Congfu Zhao Page 1 of 1

It is certified that error appears in the above-identified patent and that said Letters Patent is hereby corrected as shown below:

On the Title Page

Item [76] Inventor's name: change "Songjian" to -- Songjiang --

Signed and Sealed this
Twentieth Day of March, 2018

Andrei Iancu
*Director of the United States Patent and Trademark Office*